United States Patent [19]
Guy et al.

[11] Patent Number: 5,837,545
[45] Date of Patent: Nov. 17, 1998

[54] GENES, POLYPEPTIDES, AND COMPOSITIONS FOR COLD TOLERANCE IN PLANTS

[75] Inventors: Charles L. Guy; Dale W. Haskell, both of Gainesville; Andrea Hofig, Newberry, all of Fla.; Lisa Gail Neven, Yakima, Wash.

[73] Assignee: Research Corporation Technologies, Inc., Tucson, Ariz.

[21] Appl. No.: 7,107

[22] Filed: Jan. 21, 1993

[51] Int. Cl.[6] .......................... C07K 14/415; C12N 1/15; C12N 15/29; C12N 15/63
[52] U.S. Cl. .................. 435/419; 435/172.3; 435/243; 435/252.3; 435/255.1; 435/69.1; 435/254.2; 536/23.6; 800/205; 800/DIG. 40; 800/DIG. 38
[58] Field of Search ........................... 800/205, DIG. 38, 800/DIG. 40; 435/172.3, 240.4, 243, 252.3, 255.1, 254.2, 419, 69.1; 536/23.6

[56] References Cited

U.S. PATENT DOCUMENTS 4,797,359  1/1989  Finkelstein .............................. 435/69.1
5,071,962  12/1991  Morrison et al. ..................... 530/389.5

FOREIGN PATENT DOCUMENTS 9108292  6/1991  WIPO.

OTHER PUBLICATIONS

Guy, Charles L. (1990) "Cold Acclimation and Freezing Stress Tolerance: Role of Protein Metaboism" Annu. Rev. Plant Rhysiol. Plant Mol. Biol. 41:187–223.

Guy, Charles L., and Dale Hakell (1987) "Induction of Freezing Tolerance in Spinach Is Associated with the Synthesis of Cold Acclimation Induced Proteins" Plant Physiol. 84:872–878.

Hajela, Ravindra K., David P. Horvath, Sarah J. Gilmour, and Michael F. Thomashow (1990) "Molecular Cloning and Expression of cor (Cold–Regulatd) Genes in Arabidopsis thaliana" Plant Physiol. 93:1246–1252.

Guy, C.L., Dale Haskell, and George Yelenosky (1988) "Changes in Freezing Tolerance and Polypeptide Content of Spinach and Citrus at 5° C." Cryobiology 25:264–271.

Chen, Paul, P.H. Li, and C.J. Weiser (1975) "Induction of Frost Hardiness in Red–osier Dogwood Stems by Water Stress" HortScience 10(4):372–374.

Harada, John J., Alice J. DeLisle, Catherine S. Baden, and Marth L. Crouch (1989) "Unusual sequence of an abscisic acid–inducible mRNA which accumulates late in *Brassica napus* seed development" Plant Molecular Biology 12:395–401.

Kurkela, Sirpa, and Marianne Franck (1990) "Cloning and characterization of a cold– and ABA–inducible Arabidopsis Gene" Plant Molecular Biology 15:137–144.

Gilmour, Sarah J., Ravindra K. Hajela, and Michael F. Thomashow (1988) "Cold Acclimation in *Arabidopsis thaliana*" Plant Physiol. 87:745–750.

Hughes, D. Wayne, and Glenn A. Galau (1991) "Developmental and Environmental Inductionof Lea and LeaA mRNAs and the Postabscission Program during Embryo Culture" The Plant Cell 3:605–618.

(List continued on next page.)

Primary Examiner—David T. Fox
Assistant Examiner—Elizabeth C. Kemmerer
Attorney, Agent, or Firm—Greenlee, Winner and Sullivan, P.C.

[57] ABSTRACT

Described are proteins having molecular weights of 85 and 160 kDa, which proteins are responsive to cold acclimation or drought stress in plants. The cDNA for the 85 and 160 kDa proteins, designated CAP85 and CAP160, are disclosed. Transgenic cells, including microorganisms and plants, can be produced which express the CAP85 and CAP160 proteins and thereby advantageously enhance the cold or water stress tolerance in the transgenic organism. Freeze and desiccation damage can also be prevented by applying a cold acclimation protein to the organism needing such protection.

14 Claims, 6 Drawing Sheets

OTHER PUBLICATIONS

Raynal, Monique, Dominique Depigny, Richard Cooke, and Michel Delseny (1989) "Characterization of a Radish Nuclear Gene Expressed during Late Seed Maturation" Plant Physiol. 91:829–836.

Cattivelli, Luigi, and Dorothea Bartels (1990) "Molecular Cloning and Characterization of Cold–Regulated Genes in Barley" Plant Physiol. 93:1504–1510.

Mundy, John, Kazuko Yamaguchi–Shinozaki, and Nam–Hai Chua (1990) "Nuclear proteins bind conserved elements in the abscisic acid–responsive promoter of a rice rab gene" Proc. Natl. Acad. Sci. USA 87:1406–1410.

Hong, Bimei, Scott J. Uknes, and Tuan–hua David Ho (1988) "Cloning and charcterization of a cDNA encoding a mRNA rapidly–induced by ABA in barley aleurone layers" Plant Molecular Biology 11:495–506.

Lang, V., P. Heino, and E.T. Palva (1989) "Low terperature acclimation and treatment with exogenous abscisic acid induce common polypeptides in *Arabidopsis thaliana* (L.) Heynh" Theor. Appl. Genet. 77:729–734.

Mohapatra, Shyam S., Lawrence Wolfraim, Ronald J. Poole, and Rajinder S. Dhindsa "Molecular Cloning and Relationship to Freezing Tolerance of Cold–Acclimation–Specific Genes of Alfalfa" Plant Physiol. 89:375–380.

Vilardell, J., A. Goday, M.A. Freire, M. Torrent, M.C. Martinez, J.M. Torne, and M. Pages (1990) "Gene sequence, developmental expression, and protein phosphorylation of RAB–17 in maize" Plant Molecular Biology 14:423–432.

Nordin, Kerstin, Pekka Heino, and E. Tapio Palva (1991) "Separate signal pathways regulate the expression of a low–temperature–induced gene in *Arabidopsis thaliana* (L.) Heynh" Plant Molecular Biology 16:1061–1071.

Cloutier, Yves, and Christopher J. Andrews (1984) "Efficiency of Cold Hardiness Induction by Desiccation Stress in Four Winter Cereals" Plant Physiol. 76:595–598.

Chen, H.H., P. Gavinlertvatana, and P.H. Li (1979) "Cold Acclimation of Stem–Cultured Plants and Leaf Callus of Solanum Species" Bot. Gaz. 140(2):142–147.

Chen, Tony H.H., and Lawrence V. Gusta (1983) "Abscisic Acid–Induced Freezing Resistance in Cultured Plant Cells" Plant Physiol. 73:71–75.

Siminovitch, David, and Yves Cloutier (1982) "Twenty––Four–Hour Induction of Freezing and Drought Tolerance in Plumules of Winter Rye Seedings by Desiccation Stress at Room Temperature in the Dark" Plant Physiol. 69:250–255.

Gilmour, Sarah J., Nancy N. Artus, and Michael F. Thomashow (1992) "cDNA sequence analysis and expression of two cold–regulated genes of *Arabidopsis thaliana*" Plant Molecular Biology 18:13–21.

Gilmour, Sarah J., and Michael F. Thomashow (1991) "Cold acclimation and cold–regulated gene expression in ABA mutants of *Arabidopsis thaliana*" Plant Molecular Biology 17:1233–1240.

Yelenosky, George, and Charles L. Guy (1989) "Freezing Tolerance of Citrus, Spinach, and Petunia Leaf Tissue" Plant Physiol. 89:444–451.

Guy, Charles, Dale Haskell, Lisa Neven, Paul Kein, and Chris Smelser (1992) Hydration–state–responsive proteins link cold and drought stress in spinach Planta 188:265–270.

Dure, Leon III., M. Crouch, J. Harada, Tuan–Hua D. Ho, J. Mundy, R. Quatrano, T. Thomas, and Z.R. Sung (1989) "Common amino acid sequence domains among the LEA proteins of higher plants" Plant Molecular Biology 12:475–486.

Baker, Jean, Christopher Steele, and Leon Dure III (1988) "Sequence and characterization of 6 Lea proteins and their genes from cotton" Plant Molecular Biology 11:277–291.

Cloutier, Y. and D. Siminovitch (1982) "Augmentation of protoplasm in drought– and cold–hardened winter wheat" Can. J. Bot. 60:674–680.

McKown et al. 1990. Cryobiology 27: 659–660.

Vardi et al. 1990. Plant Sci. 69: 199–206.

Wada et al. 1990. Nature 347: 200–203.

| | |
|---|---|
| ATGAAGAAGAATAACAAGGGTGAGGATCACAAGCCATCCGAGGCCGATGT | 50 |
| M  K  K  N  N  K  G  E  D  H  K  P  S  E  A  D  V | |
| GATTGCCTCCGGCGGTATCGGAAAGTTGCCCGTCTCCGAACCTGCTCATT | 100 |
| I  A  S  G  G  I  G  K  L  P  V  S  E  P  A  H  Y | |
| ATGACCATGATGACAAGGAACATGTTGGACTCCTTGAGAAAAAACATATT | 150 |
| D  H  D  D  K  E  H  V  G  L  L  E  K  K  H  I | |
| GGACTTGTTCAGCAATTCCATCGTTCTGATCACGCTTCCGACGAAAGACA | 200 |
| G  L  V  E  Q  F  H  R  S  D  H  A  S  D  E  R  H | |
| TCATGATGAAGAGCAAAACAAAGGTGGTGTCTTCGGAAAAATCAAGGAGA | 250 |
| H  D  E  E  Q  N  K  G  G  V  F  G  K  I  E  K | |
| AGCTCCCCGGTCAGCATGATTCGGATACTACCACACATACACAACAATTA | 300 |
| L  P  G  Q  H  D  S  D  T  T  H  T  Q  Q  L | |
| TACCCTGCTTCTGATCATAACTACAACACCCACCATGTCCACCAAGACGA | 350 |
| Y  P  A  S  D  H  N  Y  N  T  H  H  V  H  Q  D  D | |
| TGAAAAGAAGGACAACATCCTTGACAAAATCAAGGATAAGCTTCCCGGAA | 400 |
| E  K  K  D  N  I  L  D  K  I  K  D  K  L  P  G  K | |
| AACACGAAGATAAGAAGCAAGACTATCACCAGCACCAAGAGGAGGAAAAG | 450 |
| H  E  D  K  K  Q  D  Y  H  Q  H  Q  E  E  E  K | |
| AAGGGAGGAGCCCTTGACAAAATCAAGGACAAGCTGCCCGGTCAGGGTAA | 500 |
| K  G  G  A  L  D  K  I  K  D  K  L  P  G  Q  G  N | |
| TGCTGGACACACGCAGCAATTATACCCTGCCCCTGATCATAACTACAACA | 550 |
| A  G  H  T  Q  Q  L  Y  P  A  P  D  H  N  Y  N  T | |
| CACACCATGTCCACCAAGACGAGGAAAACAAGGATAGTGTCTTAGACAAA | 600 |
| H  H  V  H  Q  D  E  E  N  K  D  S  V  L  D  K | |
| ATCAAGGATAAGCTGCCCGGACTACATGAGGACAAGAAGAACGACTAT | 648 |
| I  K  D  K  L  P  G  L  H  E  D  K  K  N  D  Y | |

FIG. 2

```
                             ↓
CACGAGCTAATTTGTTGTAATCAAGCAATAACAATGGCTGATGAAAGGAA           50
                                     M  A  D  E  R  N         6

CACTTATGGGGGACCCGCACCATCTATGGAGACCACTGATCGTGGTATGT          100
 T  Y  G  G  P  A  P  S  M  E  T  T  D  R  G  M  F          23

TTGATTTCATGAAGAAGAACAACAAGGGAGAGGATCACAAGCCATCCGAG          150
 D  F  M  K  K  N  N  K  G  E  D  H  K  P  S  E             39

GCCGATGTGATTGCCTCCGGCGGTATCGGAAAGTTGCCCGTCTCCGAACC          200
 A  D  V  I  A  S  G  G  I  G  K  L  P  V  S  E  P          56

TGCTCATTATGACCATGATGACAAGGAACATGTTGGACTCCTTGAGAAAA          250
 A  H  Y  D  H  D  D  K  E  H  V  G  L  L  E  K  K          73

AACATATTGGACTTGTTGAGCAATTCCATCGTTCTGATCACGCTTCCGAC          300
  H  I  G  L  V  E  Q  F  H  R  S  D  H  A  S  D            89

GAAAGACATCATGATGAAGAGCAAAACAAAGGTGGTGTCTTCGGAAAAAT          350
 E  R  H  H  D  E  E  Q  N  K  G  G  V  F  G  K  I         106

CAAGGAGAAGCTCCCCGGTCAGCATGATTCGGATACTACCACACATACAC          400
 K  E  K  L  P  G  Q  H  D  S  D  T  T  T  H  T  Q         123

AACAATTATACCCTGCTTCTGATCATAACTACAACACCCACCATGTCCAC          450
 Q  L  Y  P  A  S  D  H  N  Y  N  T  H  H  V  H           139

CAAGACGATGAAAAGAAGGACAACATCCTTGACAAAATCAAGGATAAGCT          500
 Q  D  D  E  K  K  D  N  I  L  D  K  I  K  D  K  L         156

TCCCGGGAAACATGAAGATAAGAAGCAAGACTATCACCAGCACCAAGAGG          550
 P  G  K  H  E  D  K  K  Q  D  Y  H  Q  H  Q  E  E         173

AGGAAAAGAAGGGAGGAGCCCTTGACAAAATCAAGGACAAGCTGCCCGGT          600
 E  K  K  G  G  A  L  D  K  I  K  D  K  L  P  G           189

CAGGGTAATGCTGGACACACGCAGCAATTATACCCTGCCCCTGATCATAA          650
 Q  G  N  A  G  H  T  Q  Q  L  Y  P  A  P  D  H  N         206

CTACAACACACACCATGTCCACCAAGACGAGGAAAACAAGGATAGTGTCT          700
 Y  N  T  H  H  V  H  Q  D  E  E  N  K  D  S  V  L         223

TAGACAAAATCAAGGATAAGCTGCCCGGACAACATGAAGATAAGAAGAAT          750
 D  K  I  K  D  K  L  P  G  Q  H  E  D  K  K  N           239

GACTATCACCACCACCAAGAGGAGGAAAAGAAGGATAGTGTCCTAGACAA          800
 D  Y  H  H  H  Q  E  E  E  K  K  D  S  V  L  D  K         256
```

FIG. 3A

```
AATCAAGGATAAGATGTCCGGGCAGCATGAAGATAAGAAGAATGACTATC          850
 I   K   D   K   M   S   G   Q   H   E   D   K   K   N   D   Y   H      273

ACCACCACCAAGAGGAGGAAAAGAAGGGAGGAGTCCTTGACAAAATCAAG           900
 H   H   Q   E   E   K   K   G   G   V   L   D   K   I   K           289

GACAAGTTGCCTGGTCAACATGATGCAGACACTGCCAGACACACGCAGCA           950
 D   K   L   P   G   Q   H   D   A   D   T   A   R   H   T   Q   Q      306

ACTATACCCTGCTGCTGATCATAACTACAACACACACCATGTCCACCAAG          1000
 L   Y   P   A   A   D   H   N   Y   N   T   H   H   V   H   Q   D      323

ATGAGGAAAACAAGGATAGCGTCCTTGACAAAATCAAGGACAAACTACCC          1050
 E   E   N   K   D   S   V   L   D   K   I   K   D   K   L   P          339

GGACAACATGATGATAAGGCTGCATACTCGCAACATGACCACCACAAGCA          1100
 G   Q   H   D   D   K   A   A   Y   S   Q   H   D   H   H   K   H      356

CCACCAAGAGGAGGAAAACAAGGGTGGAGTCCTCGACAAAATCAAGGACA          1150
 H   Q   E   E   N   K   G   G   V   L   D   K   I   K   D   K          373

AACTGCCTGGTGTCTACATGGTGGTCAAACATGATGGTGATATTGTCGAA          1200
 L   P   G   V   Y   M   V   V   K   H   D   G   D   I   V   E          389

CACACGCAACAATTATACCCTGCTCCTGATCATAACTACAACACTCACTA          1250
 H   T   Q   Q   L   Y   P   A   P   D   H   N   Y   N   T   H   Y      406

TGTCCATGAAGACGAGAAAAAGAAGGATAGTGTCCTAGACAAAATCAAGG          1300
 V   H   E   D   E   K   K   K   D   S   V   L   D   K   I   K   D      423

ACAAGTTACCCGGACAACATGAGGAAAAGGCAGCAGCATACTCTGAGCCA          1350
 K   L   P   G   Q   H   E   E   K   A   A   A   Y   S   E   P          439

TCATATGATTCACACCCTACACCTGCAAAGCATCATGATTATTTCCCCCA          1400
 S   Y   D   S   H   P   T   P   A   K   H   H   D   Y   F   P   Q      456

AGAGGAGGAAAAGAAAGGTGGTGTCATGGACAAAATTAAGGACAAGCTTT          1450
 E   E   E   K   K   G   G   V   M   D   K   I   K   D   K   L   S      473

CCGGCCAACATAAAGATAAGGCCGACGAGCATGAGTTGGTTGCTCCGTTG          1500
 G   Q   H   K   D   K   A   D   E   H   E   L   V   A   P   L          489

GTGACAGTCGAACCACATTCTGAGGGTGATAAGGAAAAGAAGGGGTTCTT          1550
 V   T   V   E   P   H   S   E   G   D   K   E   K   K   G   F   L      506

GGAGAAGATTAAGGACAAAATCCCCGGCCTCCACTCCAAGAATGATGCTG          1600
 E   K   I   K   D   K   I   P   G   L   H   S   K   N   D   A   E      523

AAGAGAAGAAGACCCATGAGGAGAAAAAGAGGGATACTAAACTTAACTA          1650
 E   K   K   T   H   E   E   K   K   E   G   Y   •                   535
```

FIG. 3B

| | | | | | | | | | | | | | | | | | | | |
|---|---|---|---|---|---|---|---|---|---|---|---|---|---|---|---|---|---|---|---|
| I= | H | D | E | E | Q | N | K | G | G | V | F | G | K | I | K | E | K | L | P | G | Q | H |
| II= | H | Q | D | D | E | K | K | D | N | I | L | D | K | I | K | D | K | L | P | G | K | H |
| III= | H | Q | E | E | E | K | K | G | G | A | L | D | K | I | K | D | K | L | P | G | Q | G |
| IV= | H | Q | D | E | E | N | K | D | S | V | L | D | K | I | K | D | K | L | P | G | Q | H |
| V= | H | Q | E | E | E | K | K | D | S | V | L | D | K | I | K | D | K | M | S | G | Q | H |
| VI= | H | Q | E | E | E | K | K | G | G | V | L | D | K | I | K | D | K | L | P | G | Q | H |
| VII= | H | Q | E | E | E | K | K | G | G | V | L | D | K | I | K | D | K | L | P | G | Q | H |
| VIII= | H | Q | E | E | E | N | K | G | G | V | L | D | K | I | K | D | K | L | P | G | V | Y |
| IX= | H | E | D | E | K | K | K | D | S | V | L | D | K | I | K | D | K | L | P | G | Q | H |
| X= | P | Q | E | E | E | K | K | G | G | V | M | D | K | I | K | D | K | L | S | G | Q | H |
| XI= | S | E | G | D | K | E | K | K | G | F | L | E | K | I | K | D | K | I | P | G | L | H |

CONSENSUS

[H] Q [E E E K K] G G V L [D K] I [K D K] L P G Q [H]

RESIDUE

GENES, POLYPEPTIDES, AND COMPOSITIONS FOR COLD TOLERANCE IN PLANTS

This research was supported in part by USDA Grants 85-CRCR-1-1649, CRCR-88-37264-4024, CRCR-89-37264-4024, and CSRS #90-37280-5527. The government has certain rights in this invention.

BACKGROUND OF THE INVENTION

Plants must possess and maintain adaptive mechanisms to ensure survival during periods of adverse environmental conditions. Two common stresses that temperate species are most likely to encounter are freezing and drought, both of which may cause cellular dehydration. Plants with the ability to become more freezing tolerant upon exposure to low nonfreezing temperatures in the range of 0°–10° C. contain genes that encode products which are directly or indirectly responsible for the greater resistance. Low temperature exposure and/or a change in day length may be necessary for these genes to become activated and produce gene product(s) in amounts that are physiologically significant in response to a natural environment. Once activated, proper expression of the genes confers on plant cells and tissues added resistance to the stresses and mechanical strains caused by the withdrawal of cellular water during ice formation. As long as expression of these genes continues at proper levels, and their respective products are localized at the proper cellular sites, the cells will remain tolerant to extracellular freezing at a level that is characteristic for that particular species. Once expression of the genes is reduced or halted in tolerant plants, resistance to the stresses and strains of extracellular freezing will decline. Since this increased freezing tolerance results from the process termed cold acclimation, genes responsible for the greater freezing tolerance that are induced or activated by low temperature are given the name "cold acclimation genes."

Cold acclimation constitutes an inducible response on the part of temperate plants to developing unfavorable temperature conditions. Conversely, most plants that have evolved in and are native to tropical regions of the world lack the ability to tolerate even the slightest freezing. More importantly, they lack the inducible mechanism of cold acclimation and cannot alter their freezing tolerance upon exposure to low nonfreezing temperatures. The dichotomies between temperate and tropical species in tolerance to freezing and ability to cold acclimate are the result of evolutionary pressures and natural selection as plants colonized colder regions of the world. Nevertheless, it is the activation and expression of certain genes in temperate species that is not only necessary, but is also diagnostic of greater freezing tolerance.

Specific polypeptides are induced and/or synthesized at higher rates only when certain plants and certain tissues are becoming more cryotolerant (Guy, C. L., D. Haskell [1987] *Plant Physiol.* 84:872–878; Guy et al. [1988] *Cryobiology* 25:264–271; Gilmour et al. [1988] *Plant Physiol.* 87:745–750). Similarly, these same proteins cease to be synthesized at high rates during the loss of cryotolerance at noninductive temperatures. Thus, the synthesis of these proteins shows induction and repression kinetics that exactly mimic the induction and loss of freezing tolerance (Guy and Haskell [1987], supra).

Since increases in freezing tolerance are tightly linked to the syntheses of these proteins, the ability of a given plant or tissue to show increases in freezing tolerance ultimately depends on the presence and proper expression of the genes that encode the above proteins inducible by low nonfreezing temperature exposure.

A major component of freezing tolerance appears to involve tolerance to dehydration (Yelenosky, G., C. L. Guy [1989] *Plant Physiol.* 89:444–451). Therefore, responses evoked by water stress may also be involved in freezing tolerance mechanisms. Many studies have demonstrated that a mild drought stress can increase freezing tolerance (Chen, P., P. H. Li, C. J. Weiser [1975] *Hort. Sci.* 10:372–374; Cloutier, Y., C. J. Andrews [1984] *Plant Physiol.* 76:595–598; Cloutier, Y., D. Siminovitch [1982] *Plant Physiol.* 69:256–258; Guy, C., D. Haskell, L. Neven, P. Klein, C. Smelser [1992] *Planta* 188:265–270; Siminovitch, D., Y. Cloutier [1982] *Plant Physiol.* 69:250–255) and that application of abscisic acid (ABA) at nonacclimating temperatures can also increase freezing tolerance (Chen, H. H., P. Gavinlertvatana, P. H. Li [1979] *Bot. Gaz.* 140:142–147; Chen, H. H., L. V. Gusta [1983] *Plant Physiol.* 73:71–75; Lang, V., P. Heino, E. T. Palva [1989] *Theor. Appl. Genetics* 77:729–734; Mohapatra, S. S., L. Wolfraim, R. J. Poole, R. S. Dhindsa [1988] *Plant Physiol.* 89:375–380).

A number of genes responsive to heat stress, water stress, and ABA treatments have now been characterized (U.S. Pat. Nos. 5,071,962; 4,797,359; Baker, J., C. Steele, L. Dure III [1988] *Plant Mol. Biol.* 11:277–291; Harada, J. J., A. J. DeLisle, C. S. Baden, M. L. Crouch [1989] *Plant Mol. Biol.* 12:395–401; Hong, B., S. J. Uknes, T. D. Ho [1988] *Plant Mol. Biol.* 11:495–506; Hughes, D. W., G. A Galau [1991] *Plant Cell* 3:605–618; Mundy, J., K Yamaguchi-Shinozaka, N. H. Chua [1990] *Proc. Natl. Acad. Sci. USA* 87:1406–1410; Raynal, M., D. Depigny, R. Cooke, M. Delseny [1989] *Plant Physiol.* 91:829–836; Vilardell, J., A Goday, M. A. Freire, M. Torrent, M. C. Martinez, J. M. Torne, M. Pages [1990] *Plant Mol. Biol.* 14:423–432). For simplicity of nomenclature, the group of water stress proteins is referred to as WSPs. These proteins were originally identified as LEAs, RABs, and dehydrins. LEAs (late embryogenesis abundant proteins) are, as their name implies, expressed at high levels during the latter stages of seed development and programmed seed dry-down (Dure, L. III, M. Crouch, J. Harada, T. D. Ho, J. Mundy, R. Quatrano, T. Thomas, Z. R. Sung [1989] *Plant Mol. Biol.* 12:475–486). Dehydrins and RABs (responsive to ABA) are similar to LEAs in several ways: hydrophilicity (>55% hydrophilic residues), responsiveness to ABA treatments, boiling solubility, a general absence of cysteine and tryptophan residues, and the presence of repeating motifs. Most of these proteins range in size from 10 kDa to 40 kDa.

In contrast to the water stress proteins, very little is known about proteins and genes which participate in plant freezing tolerance (Cattivelli, L., D. Bartels [1990] *Plant Physiol.* 93:1504–1510; Gilmour, S. J., N. N. Artus, M. F. Thomashow [1992] *Plant Mol. Biol.* 18:13–21; Guy, C. L. [1990]*Annu. Rev. Plant Physiol Plant Mol. Biol.* 41:187–223; Hajela, R. K, D. P. Horvath, S. J. Gilmour, M. F. Thomashow [1990] *Plant Physiol.* 93:1246–1252; Kurkela, S., M. Franck [1990] *Plant Mol. Biol.* 15:137–144). Recent findings indicate that WSP-like proteins may also participate in plant freezing tolerance (Gilmour, S. J., M. F. Thomashow [1991] *Plant Mol. Biol.* 17:1233–1244; Gilmour et al.[1992], supra; Nordin, K., P. Heino, E. T. Palva [1991] *Plant Mol. Biol.* 16:1061–1071), but the nature of their role in this process remains uncertain.

SUMMARY OF THE INVENTION

The subject invention concerns nucleotide sequences that encode either inducible or upregulated (increased synthesis and accumulation) proteins during exposure to low temperature or under drought stress. Specifically described herein are cDNA sequences encoding the proteins designated CAP85 and CAP160. The subject nucleotide sequences or genes comprising those sequences can be utilized to create transgenic plants having the advantageous characteristics of cold tolerance or drought resistance. These DNA sequences can also be used as probes in assays for crop and plant tolerance levels during seasons of risk to freezing temperature or drought conditions.

Also disclosed are proteins that are encoded by the disclosed genes. These proteins can be employed in novel methods for preventing freeze damage or desiccation damage to a cell, including plant cells and eukaryotic and prokaryotic organisms. Monoclonal antibodies that specifically recognize the disclosed proteins are also described. Further, the subject invention concerns transgenic plants which have been transformed with the subject genes in order to express the described proteins, thereby enhancing the freezing tolerance or drought resistance of the transformed host.

BRIEF DESCRIPTION OF THE DRAWINGS

FIG. 2 shows the sequence of CAP85 PCR clone pcr733 (SEQ ID NOS: 1 and 2). The positions of the synthetic oligonucleotides which were used to amplify the pcr733 fragment from cDNA are shown in boxes.

FIGS. 3A and 3B show the sequence of the 1.8 kb cDNA clone of CAP85 (SEQ ID NOS: 1 and 2). The sequence of pcr733 is identical to the 5' region, 110–850 bp of the cDNA clone. The arrow above the first methionine of the cDNA indicates a translation start site consensus sequence. Repeating motifs are noted as follows: boxed, lysine rich 22-mer; single underline, 16-mer; double underline, 8-mer.

FIG. 4 lists the 11 repeats of the 22 amino acid lysine-rich motif (SEQ ID NO:2). The residue notations are: p, polar; +, positively charged; –, negatively charged; n, nonpolar; g, glycine. Charged residues are boxed in the consensus sequence.

BRIEF DESCRIPTION OF THE SEQUENCES

Figure 1:
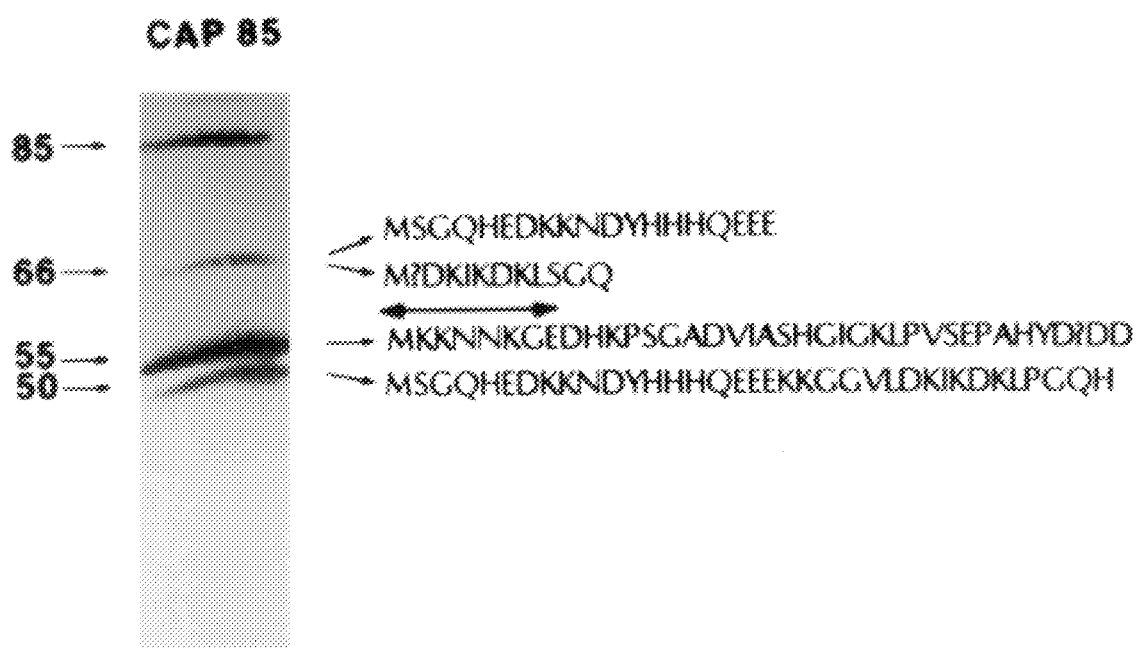
FIG. 1. Peptide sequences of CAP85(SEQ IN NO:2). CAP85 was cleaved by CNBr and the peptides were resolved by SDS-PAGE. Three major peptides of 66, 50, and 55 kDa were sequenced using gas-phase amino acid sequencing.

SEQ ID NO. 1 is the nucleotide sequence for CAP85

SEQ ID NO. 2 is the deduced amino acid sequence of CAP85.

SEQ ID NO. 3 is the nucleotide sequence for CAP160.

SEQ ID NO. 4 is the deduced amino acid sequence of CAP160.

SEQ ED NO. 5 is degenerate synthetic oligonucleotide primer 55-A5', constructed from the peptide sequence of the CNBr peptides.

SEQ ID NO. 6 is degenerate synthetic oligonucleotide primer 50-B3', constructed from the peptide sequence of the CNBr peptides.

DETAILED DESCRIPTION OF THE INVENTION

The subject invention concerns materials and methods for protecting cells against damage that can result from low temperatures or desiccation. Specifically, the invention described herein provides proteins that are useful in procedures for making cells more resistant to cold or drought. Genes encoding these proteins are also provided.

As disclosed herein, the proteins of the subject invention can be purified by preparative electrophoretic methods, and polyclonal and monoclonal antibodies made to the purified proteins. The proteins may also be produced by recombinant means. Specifically described herein are the CAP85 and CAP160 proteins and the genes encoding these proteins.

CAP85. CAP85 is a basic protein with an apparent molecular weight of about 85 kDa in 10% acrylamide gels and exhibiting a pI of about 6.3 in isoelectric focusing gels. The protein is present in spinach leaf tissue and hypocotyl. The MIRNA for CAP85 does not appear to encode a signal sequence or a precursor protein for transport into organelles. The gene(s) are encoded in the nucleus, and the protein is synthesized on cytoplasmic ribosomes. The DNA sequence for CAP85 was determined and is shown herein as SEQ ID NO. 1. The corresponding amino acid sequence is shown in SEQ ID NO. 2. Several partial amino acid sequences derived from cyanogen bromide cleavage fragments have also been determined. Western blot analyses indicate an 85 kDa molecular weight protein is present in non-acclimated leaf tissue at low levels, but is accumulated when plants are grown at 5° C. Like the CAP160 protein, we have found that this protein is also accumulated in leaf tissue subjected to desiccation.

CAP85 is regulated in response to low temperature and is also responsive to slight changes in water balance. CAP85 accumulates during exposure to low temperature or water stress. In the experiments described herein, the soil was well-watered and the plants did not show any loss of turgor or decrease in water potential. Therefore, the accumulation of CAP85 during cold acclimation does not appear to be due to water stress, but represents a true low temperature response.

CAP160 . CAP160 is an acidic protein with an apparent molecular weight of about 155 to about 160 kDa in 10% SDS acrylamide gels and also exhibits a pI of about 4.5 to 4.7 in isoelectric focusing gels. This protein is present in spinach leaf and hypocotyl tissue and can be resolved into as many as five physically similar isoforms varying only slightly in pI and molecular weight. This protein is phosphorylated. The protein is not accumulated in the nucleus, chloroplast, or mitochondria of the cell. It is encoded by a nuclear gene(s) and is synthesized on cytoplasmic ribosomes. The mRNA does not encode a precursor translation product exhibiting a leader sequence for transport into organelles. The DNA sequence for the gene encoding the CAP160 protein is shown as SEQ ID NO. 3. The amino acid sequence of the protein is shown as SEQ ID NO. 4. Partial amino acid sequences have been derived from cyanogen bromide cleavage fragments of the protein. This protein, or similar homologues, may be present in a number of plant species including *Citru, Poncirus, Petunia,* and *Arabidopsis.* Western blot experiments, using mouse hybridoma cell culture supernatants, demonstrate that this protein is present in nonacclimated spinach leaf and hypocotyl tissue, and is accumulated during exposure to 5° C. This protein is also accumulated in droughted or desiccated leaf and hypocotyl tissue.

The amino acid compositions for each of the described proteins was determined and compared in Table 1. Proteins from cold acclimated hypocotyl tissue were separated by two-dimensional gel electrophoresis and electroblotted onto PVDF. Individual proteins were excised, hydrolyzed, and the liberated amino acids were determined by HPLC.

TABLE 1

Amino acid composition of high molecular mass cold acclimation proteins from spinach hypocotyl tissue

| Amino acid | Composition (mol %) | |
|---|---|---|
| | 160 kDa | 85 kDa |
| Asparagine/aspartic | 12.4 | 16.2 |
| Threonine | 9.8 | 3.8 |
| Serine | 10.6 | 4.9 |
| Glutamine/glutamic | 15.3 | 16.4 |
| Proline | 5.2 | 5.0 |
| Glycine | 14.8 | 8.5 |
| Alanine | 7.0 | 5.8 |
| Methionine | 1.4 | 0.4 |
| Isoleucine | 3.6 | 2.9 |
| Leucine | 4.3 | 5.8 |
| Histidine | 4.6 | 9.3 |
| Lysine | 7.2 | 12.9 |
| Valine | 1.8 | 3.0 |
| Tyrosine | 0.5 | 3.8 |
| Phenylalanine | 0 | 0.6 |
| Arginine | 1.3 | 0.7 |

The cDNA transcript can be obtained from the plasmids in essentially pure form by standard art methods. The essentially pure cDNA thus obtained can be used for subcloning into a different transformation vector.

Introduction of a single or multiple genes into plants and appropriate expression can lead to an increase in cold tolerance or drought resistance in the transformed plant. The described transformations center around introduction of the genes using engineered Ti plasmid vectors in *Agrobacterium tumefaciens*. Model libraries containing but a single cold acclimation gene, and all possible combinations of several cold acclimation genes can be used to transform freezing sensitive plants. Expression of the genes can be controlled by a number of promoters ranging from the 35S promoter of cauliflower mosaic virus to a number of inducible promoters where the expression of the introduced genes can be controlled by the external application of an environmental condition or chemical. Alternatively, the natural upstream promoter regions of the cold acclimation genes can be used to control expression of the cold acclimation genes in transgenic plants upon exposure to low temperatures. However, it may be necessary to introduce the genes for the transacting factors that recognize the cold acclimation consensus elements of the cold acclimation gene promoters, provided that freezing sensitive plants, in general, lack genes responsive to low temperature.

The creation of transformed plants can utilize any one of several strategies well known in the art for introduction of foreign genes into cold sensitive plants, including electroporation and facilitated DNA uptake (protoplast and liposome fusion) (Fromm et al.[1986] *Nature* 319:791), the biolistic gun, and with Agrobacterium (Horsch et al.[1985] *Science* 227:1229–1231). At the present time, transformation with Agrobacterium is the most versatile method available.

Inoculations of plant tissues to be transformed by Ti plasmid transfer can be made with *Agrobacterium tumefaciens* strains carrying cointegrates of disarmed Ti plasmid constructs encoding genes for antibiotic resistance and a spinach cold acclimation gene. The bacterial strains and transformation vectors have been described and are well known in the art.

The proteins described herein can be used to protect a cell from freeze damage or desiccation damage brought on by the formation of intracellular or extracellular ice. For example, the protein can be added, with an appropriate carrier, directly to the plant by applying it to the surface or injected into the plant or can be placed in the growth medium of the plant. Appropriate carriers, preservatives, and adjuvants are well known in the art and can be readily adapted for each particular protein or plant.

As is well known in the art, the amino acid sequence of a protein is determined by the nucleotide sequence of the DNA Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

Phenylalanine (Phe) TTK Histidine (His) CAK
Leucine (Leu) X TY Glutamine (Gln) CAJ
Isoleucine (Ile) ATM Asparagine (Asn) AAK
Methionine (Met) ATG Lysine (Lys) AAJ
Valine (Val) GTL Aspartic acid (Asp) GAK
Serine (Ser) QRS Glutamic acid (Glu) GAJ
Proline (Pro) CCL Cysteine (Cys) TGK
Threonine (Thr) ACL Tryptophan (Trp) TGG
Alanine (Ala) GCL Arginine (Arg) WGZ
Tyrosine (Tyr) TAK Glycine (Gly) GGL
Termination signal TAJ
Termination signal TGA Key: Each 3-letter deoxynucleotide triplet corresponds to a trinucleotide of MRNA, having a 5'-end on the left and a 3'-end on the right. All DNA sequences given herein are those of the strand whose sequence corresponds to the mRNA sequence, with thymnine substituted for uracil. The letters stand for the purine or pyrimidine bases forming the deoxynucleotide sequence.

A=adenine
G=guanine
C=cytosine
T=thymine
X=T or C if Y is A or G
X=C if Y is C or T
Y=A, G, C or T if X is C
Y=A or G if X is T
W=C or A if Z is A or G
W=C if Z is C or T
Z=A, G, C or T if W is C
Z=A or G if W is A
QR=TC if S is A, G, C or T; alternatively
QR=AG if S is T or C
J=A or G
K=T or C
L=A, T, C or G
M=A, C or T The above shows that the amino acid sequences of CAP85 or CAP160 can be prepared by nucleotide sequences other than those disclosed. Functionally equivalent nucleotide sequences encoding the novel amino acid sequences of these proteins and fragments can be prepared by known synthetic procedures. Accordingly, the subject invention includes such functionally equivalent nucleotide sequences.

The one-letter symbol for the amino acids used above is well known in the art. For convenience, the relationship of the three-letter abbreviation and the one-letter symbol for amino acids is as follows:

| Ala | A | Leu | L |
| Arg | R | Lys | K |
| Asn | N | Met | M |
| Asp | D | Phe | F |
| Cys | C | Pro | P |
| Gln | Q | Ser | S |
| Glu | E | Thr | T |
| Gly | G | Trp | W |
| His | H | Tyr | Y |
| Ile | I | Val | V |

Thus, the scope of the subject invention includes not only the specific nucleotide sequences depicted herein, but also all equivalent nucleotide sequences coding for molecules with substantially the same biological activity. The term "equivalent" is being used in its ordinary patent usage here as denoting a nucleotide sequence which performs substantially as the nucleotide sequence identified herein to produce molecules with substantially the same biological activity in essentially the same kind of hosts. Within this definition are subfragments which have freezing tolerance and drought resistance biological activity.

It is well within the skill of those in the genetic engineering art to use the nucleotide sequences encoding the described environmental stress resistance activity of the subject invention to produce the disclosed proteins via microbial processes. Fusing the sequences into an expression vector and transforming or transfecting into appropriate hosts are standard procedures used in producing other well-known proteins, e.g., insulin, interferons, human growth hormone, and the like. Similar procedures, or obvious modifications thereof, can be employed to prepare proteins by microbial means or plant or mammalian tissue culture technology in accord with the subject invention.

Further, the scope of the subject invention is intended to cover not only the specific amino acid sequences disclosed, but also similar sequences of proteins or protein fragments having comparable biological activity.

MATERIALS AND METHODS

Plant material. Spinach seedlings (*Spinacia oleracea* L. cv Bloomsdale) were grown from seed in a controlled environment as previously described (Guy and Haskell [1987], supra). Cold acclimation, deacclimation, and water stress treatments were conducted as previously described (Id.).

Protein extraction. Protein was extracted from etiolated spinach (*Spinacia oleracea* L. cv Bloomsdale) hypocotyl-cotyledon tissue grown at 5° C. for 4 weeks. Frozen tissue was ground in a dry-ice-cooled mortar. Forty grams of tissue was homogenized in a Polytron with 100 ml of 80% v/v distilled phenol buffered with 120 mM Tris-HCl (pH 6.8), 50 mM EDTA, 100 mM KCl, 2% v/v Triton X-100, 5% v/v glycerol, and 2% v/v 2-mercaptoethanol was added to an additional 100 ml of the preceding buffer. The extract was centrifuged at 15,000 g for 5 minutes. The aqueous phase was removed and the phenol phase extracted with 50 ml buffer 3 additional times. The final phenol phase was filtered through glass wool to remove cellular debris. Protein was precipitated from the phenol solution with 5 volumes of −20° C. acetone containing 1% v/v 2-mercaptoethanol for 2 hours at −20° C. and pelleted at 15,000 g for 5 minutes to remove insoluble material. The supernatant was stored at −20° C. All protein content determinations were by the dye-binding method.

Protein purification. Total protein extracts were fractionated by preparative, free solution isoelectric focusing (Rotofor™, BioRad). Rotofor solution with 2% v/v ampholytes (0.8% pH 5–7, 0.8% pH 4–6, and 0.4% pH 3–10) (BioRad) was prefocused for 1 hour at 12 W constant power with 10° C. coolant. The protein sample was dissolved in Rotofor solution with 2% ampholytes (usually 3.5 to 4.0 ml containing from 31 to 187 mg of protein). The protein/ampholyte solution was loaded into the compartment having a pH near the midpoint of the gradient (to substantially eliminate protein precipitation during focusing). Proteins were focused for 5 hours at 12 W constant power with 10° C. coolant. After sample collection, 25 μl of each fraction was loaded directly onto, and separated in, 10% SDS-polyacrylamide gels. Separated proteins were stained with Coomassie blue. The free solution isoelectric focusing purification closely approximated analytical two-dimensional separations for spinach cold acclimation proteins, which facilitated identification of fractions containing CAP85. Total protein content was assayed and the percentage of CAP85 present in the fraction was determined by densitometry of the SDS-polyacrylamide gel separation, which yielded an estimate of the micrograms of CAP85 present. Protein from fractions containing CAP85 were precipitated with 5 volumes of −20° C. acetone with 1% 2-mercaptoethanol for 2 hours at −20° C. followed by centrifugation at 11,000 g. The co-precipitating urea was removed by washing with 10 ml of methanol. After centrifugation, the methanol-urea supernatant was discarded and the protein pellet dried under vacuum.

Monoclonal antibody production. Protein pellets from fractions of free solution isoelectric focusing containing CAP85 were resuspended in phosphate buffered saline. Balb/c mice were injected with approximately 100 μg of CAP85 (500 μg total protein) with RIBI MPL+TDM adjuvant. The four boosts of antigen in adjuvant were made with equal or greater amounts of antigen. Serums were titered and cell fusion supernatants were screened by Western blot of SDS-PAGE fractionated spinach proteins using a miniblotter (Immunetics). Immune complexes were detected using alkaline phosphatase conjugated to goat anti-mouse IgG. The color development substrate was NBT/BCIP.

Polyclonal antibody production. A 3 ml solution containing approximately 2400 μg total protein and about 500 μg of CAP85 was fractionated on a SDS-polyacrylamide gel (7.5%, 0.75 mm thick, 16 cm wide). After briefly staining with Coomassie blue and destaining, the CAP85 band was excised, rinsed in water 2 minutes, and homogenized with PBS in a Ten Broeck tissue grinder. The homogenized gel was transferred with water to a glass tube and lyophilized to reduce the volume of liquid. A Balb/c mouse was injected initially with 70 μg of CAP85 in RIBI MPL+TDM adjuvant. This was followed by three boosts of 70, 70, and 100 μg of CAP85 in adjuvant. The final working titer was 1:10,000.

Protein cleavage, sequencing, and homology. Initial attempts to sequence CAP85 revealed that the amino terminus was blocked. Amino acid composition suggested that the methionine content was low. Therefore, CAP85 was cleaved at methionine residues with CNBr to obtain internal peptides which could be sequenced. Protein pellets from enriched CAP85 fractions resulting from free solution isoelectric focusing were redissolved in SDS sample buffer. The protein was loaded onto a 7.5% SDS-polyacrylamide slab gel (0.75 mm thick and 16 cm wide) that had been pre-run with 0.1 mM Na thioglycolate in the cathode buffer until the front was at least 1 cm into the running gel. The proteins were transferred by semi-dry electroblotter to PVDF membrane. Without allowing the blot to dry, the CAP85 band was excised and cut into pieces to fit into a 1.5 ml microfuge tube. In the fume hood, 1 ml of 70% formic acid (diluted with distilled water from 90% formic acid) was added to the tube followed by 100 µl of 5M CNBr in acetonitrile. The closed tube was sealed from parafilm, wrapped in foil, and placed on a rocker table. A nitrogen atmosphere was not necessary for CNBr cleavage in the small tube. The reaction was allowed to proceed for 14 hours, then the tube was opened in the hood to vent gases. Formic acid was removed by lyophilization. The solution was transferred to a 15 ml Corex tube and diluted with 3 ml of distilled water, frozen at −80° C. and lyophilized overnight. When dry, another 1 ml of distilled water was added to dissolve the residue, then lyophilized again to dryness. The peptide fragments were dissolved in SDS sample buffer. After protein determination, the fragments were fractionated on 10 and 15% SDS-polyacrylamide gels that had been pre-run as before with 0.1 mM Na thioglycolate in the cathode buffer. The protein fragments, along with molecular weight standards, were transferred to PVDF using a semi-dry electroblotter. The membrane was washed twice with distilled water to remove glycine and stained with 0.2 amido black in distilled water and then destained by repeated washing with distilled, deionized water ($ddH_2O$). When dry, the membranes were stored at −20° C. until the fragments were sequenced. Protein sequencing was performed on an Applied Biosystems gas phase sequenator.

Boiling stability. Proteins were homogenized from 1.0 g of 2 day cold acclimated spinach leaf tissue in 2.0 ml of 50 mM MOPS, pH 7.5, 10 mM $MgCl_2$, 1 mM EDTA buffer in a glass tissue grinder held on ice. The homogenate was centrifuged at 15,000 g in a microfuge for 10 minutes. An aliquot of the supernatant was subjected to 100° C. heat treatment for 2 or 10 minutes. The boiled sample was centrifuged at 15,000 g for 5 minutes to remove insoluble proteins. Equal volumes, 15 µl, of total extract and boiled samples were electrophoresed on a 8.0% SDS-PAGE. Proteins were then electroblotted onto PVDF membrane and probed with the appropriate antibodies or stained with Coomassie blue.

Cell fractionations and protein extractions. Plants were cold acclimated at least 7 days prior to fractionations. All isolation steps were performed on ice or at 4° C. Final fractionation extracts were boiled for 2 minutes, centrifuged for 10 minutes at 15,000 g, transferred to new tubes, and stored at −20° C. Protein content was determined by dye-binding method.

Chloroplasts. Chloroplasts were isolated using a modification of the protocol of Cline (Cline, K. [1975] "Purification of inner and outer chloroplast envelope membranes," *In Modem Methods of Plant Analysis New Series Volume 1: Cell Components*, H. F. Linskens, J. F. Jackson, eds., Springer-Verlag, Berlin-Heidelberg). Plants were kept in the dark for at least 24 hours before isolating chloroplasts to reduce the size of starch grains that interfere with recovery of intact chloroplasts. Spinach leaf tissue, 5 g, was homogenized in 20 ml 1×HSB (homogenization solution with BSA, modified to 0.5M sorbitol to isotonically stabilize cold acclimated chloroplasts) with a Polytron using three 5–7 second bursts at setting 12. The homogenate was filtered through a cotton plugged syringe and divided between two 15-ml Corex tubes that were centrifuged for 2 minutes at 2,500 g in Beckman JA 13.1 rotor. The pellets were resuspended in 0.5 ml of 1×HS and layered on Percoll gradients that were formed by mixing 5 ml of Percoll and 5 ml of 2×HSB in plastic tubes centrifuged at 43,000 g for 30 minutes in a JA 20 rotor. Chloroplast suspensions were layered on the preformed gradients and centrifuged for 30 minutes at 1,000 g in a JA 13.1 rotor. The band of intact chloroplasts from the gradient was pooled and diluted with 2 volumes of 1×HS (homogenization solution). Chloroplasts were recovered by centrifugation in a JA 13.1 rotor at 2,000 g for 7 minutes. The chloroplast pellet was resuspended in 320 µl HS, to which was added 80 µl of proteinase K (Boehringer Mannheim) (1 mg/ml HS). After 30 minutes on ice, the proteinase K was inactivated by bringing the solution to 2 mM PMSF. The suspension was centrifuged at 1,500 g for 6 minutes in a JA 13.1 rotor and the resultant chloroplast pellet was washed with buffer. Protein from the chloroplast pellet was extracted following the addition of 30 µl of 8 mM PMSF and 90 µl of 1×SDS buffer.

Nuclei. Nuclei were isolated in Honda medium (HM). Nuclei were further purified using a modification of the Percoll step gradient. See Luthe, D. S., R. S. Quatrano (1980) *Plant Physiol.* 65:305–308. Two aliquots of 7 to 8 g of tissue were placed in a glass Petri dish on ice. HM (with 1 mM DTT substituted for the 2% 2-mercaptoethanol) was added in a ration of 3 to 1 (v/w). The tissue was chopped with a razor blade for 10 minutes. The chopped material was filtered through a coarse screen followed by a fine screen (mesh size not known). Twice, the tissue residue was returned to the Petri dish, washed with 10 ml of HM, and refiltered. The filtrate was centrifuged at 1,000 g for 5 minutes in Beckman JA 13.1 swinging bucket rotor in 30 ml Corex tubes. The pellet was resuspended in 5 ml HM in 15 ml Corex tubes and the centrifugation step repeated. The resulting pellet was resuspended in 2 ml of HM.

The HM suspensions were layered on discontinuous gradients of Percoll containing the following steps: 2 ml 40%, 2 ml 60%, and 4 ml 80% (v/v) Percoll made with gradient buffer (0.25M sucrose, 25 mM Tris-HCl, pH 7.4, 10 mM $MgCl_2$). The gradients were centrifuged at 3,948 g in a JA 13.1 swinging bucket rotor for 30 minutes. The interfaces of the 40% and 60% Percoll steps were collected and transferred to 15 ml Corex tubes and mixed with 5 ml HM. The suspensions were centrifuged for 5 minutes at 5,685 g in a JA 13.1 rotor. The supernatants were aspirated off and each pellet was resuspended in 50 µl gradient buffer and transferred to microfuge tubes. The Corex tubes were rinsed with 25 µl more of buffer and the rinses added to the microfuge tubes. The Corex tubes were rinsed with 25 µl more of buffer and the rinses added to the microfuge tubes. The presence of nuclei was confirmed by light microscopy. Protein was extracted from the nuclei by adding 50 µl of 2×SDS buffer, which formed a viscous solution, and vortexed. Protein extracts from several gradient purifications were pooled.

Mitochondria. Spinach was grown in the dark to produce etiolated hypocotyls. Four aliquots of 5 g of hypocotyl tissue were chopped for 10 minutes with razor blades in glass Petri dishes on ice containing 15 ml each of chopping medium (CM) (0.3M mannitol, 1 mM EDTA, 30 mM MOPS-KOH (pH 7.2), and 0.02% defatted BSA (w/v). The solutions of chopped tissue were individually filtered through a coarse screen followed by a fine screen into 50 ml plastic tubes. The tissue residue was returned to the Petri dish, washed with 10 ml CM, filtered into the plastic tubes, and the process repeated with 5 ml CM. The filtered suspensions were centrifuged at 3,000 g for 5 minutes in a Beckman JA rotor. The pellets were resuspended with 1.0 ml CM and layered on discontinuous Percoll gradients in 15 ml Corex tubes containing the following steps: 4 ml 13.5%, 4 ml 21%, and 2 ml 45% (v/v) Percoll made with gradient buffers of Jackson et al. (Jackson, C., J. E. Dench, D. O. Hall, A. L. Moore [1979] *Plant Physiol.* 64:150–153). The gradients were centrifuged for 30 minutes at 7,500 g in a JA 20 rotor. Fractions from the interface of the 21% and 45% steps from each of the two gradients were mixed with 20 ml of chopping medium minus BSA (CM-BSA) in 30 ml Corex tubes and centrifuged at 11,000 g for 15 minutes. After aspiration of most of the supernatant, loose pellets were transferred to microfuge tubes and spun in JA 18.1 at 11,000 g for 15 minutes. Supernatant was removed with a Pasteur pipet. Eighty microliters of CM-BSA and 20 µl of proteinase K (1 mg/ml CM-BSA) were added to the pellet. After 30 minutes on ice, the suspension was brought to 2 mM PMSF, mixed, and centrifuged in a JA 18.1 rotor at 11,000 g for 15 minutes. The supernatant was removed and the pellet was washed with 150 µl CM-BSA followed by centrifugation as above. The supernatant was removed. To the pellet, 60 µl of 8 mM PMSF in CM-BSA and 90 µl 1×SDS buffer were added with mixing by vortex mixer.

Endoplasmic reticulum. Three grams of leaf tissue were ground with a mortar and pestle with 2 vol (w/v) of grinding buffer (10 mM Tris-HCl, pH 8.5 at 25° C., 7.2% sucrose (w/v), 10 mM KCl, 5 mM $MgCl_2$). The solution was centrifuged at 10,000 g for 5 minutes in a JA rotor. The supernatant was layered on a discontinuous sucrose gradient of modified grinding buffer: 0.8 ml 0.5M, 0.8 ml 1.0M, 0.8 ml 1.5 M, 0.4 ml 2.0M sucrose. The gradients were centrifuged at 80,000 g in a SW 50.1 rotor for 30 minutes. The recovered endoplasmic reticulum fraction from the interface of the 1.0 M and 1.5 M sucrose layers was mixed with 10 ml of grinding buffer minus sucrose (GB-S) and centrifuged in a JA 20 rotor for 1 hours at 37,000 g. The pellet was resuspended in 900 µl of GB-S and 100 µl of 1.5 mg/ml GB-S stock proteinase K After 30 minutes on ice, the suspension was brought to 2 mM PMSF and centrifuged in a JA 18.1 rotor for 1 hour at 37,000 g. The pellet was mixed in 100 µl of 1×SDS buffer.

Soluble protein. After the ultracentrifugation step in the endoplasmic reticulum isolation procedure, the sample layer at the top was recovered and deemed the soluble protein fraction. One volume of this fraction was mixed with one volume of 2×SDS sample buffer.

Leaf and hypocotyl protein. Protein was extracted separately from cold acclimated leaf and hypocotyl tissue in SDS buffer and processed as above. Since CAP85 has no known enzymatic activity and can only be detected by antibody reactivity, marker proteins for selected cell fractions were assayed by protein blotting. The chloroplast marker was a polyclonal antibody reactive against the large subunit of RuBisCo purchased from Sigma. For ER, a polyclonal antibody specific for the tobacco ER luminal protein, BiP, was used. The mitochondrial marker was a polyclonal antibody reactive against the α-subunit of the $F_1$-ATPase of yeast, and the nuclear marker was an antibody reactive against high mobility group proteins.

Equal amounts of protein (3 µg/lane) were fractionated on SDS-PAGE gels and marker proteins detected by antibody binding and color visualization as described previously.

Nucleic acid purification. RNA was extracted from spinach tissues using the phenol/LiCl procedure. Poly ($A^+$) RNA was purified using oligo dT-cellulose and used in RNA blots and cDNA synthesis. DNA was extracted from spinach leaf tissue following methods known in the art.

RNA and DNA blotting. RNA blots were performed using total or poly ($A^+$) RNA DNA blots were performed using 20 µg of spinach total DNA digested with 10×excess restriction endonuclease. The digested DNA was electrophoresed in 0.8% agarose gels in TBE. The gels were then pressure blotted to Hybond-N nylon membrane (Amersham) and fixed with UV light (Stratalinker 1800, Stratagene). Both RNA and DNA blots were prehybridized in 50% formamide, 5×SSPE, 5×Denhardts, 0.2% SDS, 10 µg/ml salmon sperm DNA at 42° C. for at least 4 hours. DNA used in both blotting procedures was labeled using random primers as previously described (52). Blots (11.5×12.5 cm) were hybridized with $2 \times 10^7$ cpm, of labeled probe (approximately $5 \times 10^5$ cpm/ng), overnight at 42° C., then washed twice in 2×SSC, 0.2% SDS for 15 minutes at room temperature, followed by 2 washes in 0.5×SSC, 0.2% SDS for 30 minutes at 68° C., and 2 washes in 0.1×SSC, 0.2% SDS for 15 to 30 minutes at 68° C. Blots were wrapped wet in plastic, and placed into cassettes and exposed XAR5 X-ray film with one intensifying screen at −80° C.

Library construction and screening. A PCR fragment specific for CAP85 was generated from cDNA synthesized from 2 day cold acclimated spinach leaf tissue poly ($A^+$) RNA. Synthetic oligonucleotides matching 50 (50-B3') and 55 (55-A5') kDa CNBr peptide sequences were used to amplify cDNA. Approximately 1/10 of a cDNA synthesis reaction from an initial 2 µg poly (A+) RNA was used in the amplification reaction. The amplification of cDNA with the synthetic oligonucleotides was performed following a cycling regime of an initial denaturation of 3 minutes at 94° C., followed by 40 cycles of 1 minute 94° C., 1 minute 50° C., 3 minutes 72° C., and finishing with a final 10 minute extension at 72° C. From PCR, a 650 bp fragment was purified and blunt end cloned into EcoRV-digested Bluescript (Stratagene). cDNA synthesis for library construction, using RNA from 2 day cold acclimated leaf tissue, was performed with the Uni-Zap unidirectional lambda phage cloning kit (Stratagene). The library was screened using the PCR generated clone for CAP85. DNA sequencing was accomplished by the Taq DyeDeoxy™ Terminator Cycle Sequencing Kit (Applied Biosystems, Inc.) on an automated sequencer (Applied Biosystems, Inc.).

Sequence analysis and homology searches. Analysis of DNA sequences was initially carried out using DNASTAR (DNASTAR, Inc.). Searches of gene data bases (GENEBANK, EMBL, NBRF) and protein data bases (PIR and Swissprot) were carried out using GCG (Genetics Computer Group), which allows comparisons of DNA and peptide sequences.

Following are examples which illustrate procedures, including the best mode, for practicing the invention. These examples should not be construed as limiting. All percentages are by weight and all solvent mixture proportions are by volume unless otherwise noted.

EXAMPLE 1—CAP85 Protein and Gene Characterization

The influence of acclimation and deacclimation on CAP85 content in leaves was determined by protein blot analyses. Protein levels were elevated throughout the cold acclimation period and decreased following a return to 25° C. There were significant levels of CAP85 one day after a return to 25° C. After 7 days of deacclimation, the levels of CAP85 were near that of the non-acclimated control. CAP85 was resolved into a doublet of 85 kDa and a lower band of ≠80–84 kDa. This doublet was observed with both polyclonal and monoclonal antibodies. When protease inhibitors for the four major classes of proteases were included in the extraction buffer, the doublet pattern was not altered, nor was the intensity of the lower band reduced.

The protein used in antibody production and sequencing was composed of the doublet. Initial attempts to sequence the amino terminus from 2-D gel electroblots indicated a blocked amino terminus blockage. Amino acid composition analyses showed the presence of 0.4 mole % methionine (see Table 1), which made feasible the cleavage of CAP85 with cyanogen bromide. From this procedure, we obtained three major peptides of 66, 55, and 50 kDa, which yielded the sequences shown in FIG. 1. Peptide sequence analysis indicated homology of the 50 kDa peptide to Group 2 LEAs.

PCR cloning and cDNA library screening. The NH$_2$ terminus of CAP85 is blocked. The peptide sequence of the CNBr peptides were used to construct degenerate synthetic oligonucleotides (55-A5'=ATG AAG AAG AA(T or C) AA(C or T) AAG GG(C or T) GAG [SEQ ID NO. 5]; and 50-B3'=TA(A or G) TC(A or G) TTC TTC TT(A or G) TCC TC(A or G) TG [SEQ ID NO. 6]) primers for the PCR amplification of cDNA derived from RNA extracted from 2 day cold acclimated leaf tissue. From this procedure, a 650 bp fragment (pcr733) was amplified, cloned, and labeled for use in RNA blot analyses. This fragment hybridized to a 2-0 to 2.2 kb RNA which was upregulated during cold acclimation. The deduced amino acid sequence of this fragment showed high homology to the amino acid sequences of the 55 kDa CAP85 CNBr cleavage peptide, matching perfectly 35 of 37 identified residues (FIG. 2). A screening of 100,000 plaques with the PCR fragment yielded 60 positives, of which the two largest clones were about 1.8 kb. Both clones hybridized to a strongly upregulated message during cold acclimation. There was a large increase in the level of message after one day of exposure to 5° C. and the high levels of message were maintained over a 7-day exposure to 5° C. Upon return to 25° C., the message levels returned to that of non-acclimated plants and remained low throughout the deacclimation period. Sequencing demonstrated that the two clones were identical, except the smaller clone was missing approximately 200 bp from the 5' end (FIGS. 3A–3B ). Over 178 bp of the 3' end were non-coding sequences. Sequence analysis indicated that the cDNA clones were identical to the PCR clone. At this stage, additional matches between the deduced protein sequence of the cDNAs and the peptide sequences became evident. The 55 kDa peptide matches the cDNA predicted sequence beginning at bp 109. A peptide fragment of this size can be deduced from the cDNA. One of the 66 kDa peptide sequences was identical to that of the 50 kDa peptide. Both were perfect matches to sequences in the cDNA beginning at bp 814. The second 66 kDa peptide sequence most closely matched a sequence near the carboxyl-terminus of the cDNA beginning at bp 1474. However, it clearly cannot be the source of the 66 kDa peptide.

A consensus translation start sequence is observed at the first ATG. The predicted size of the protein encoded by the cDNA clone is 61.5 kDa. This is roughly 72% of the estimated size of CAP85 as determined by SDS-PAGE. However, the SDS-PAGE size estimates for many WSPs is usually greater than that predicted by DNA sequences. The predicted protein from the cDNA clone gives a calculated pI of 6.2, close to the estimated pI of 6.3 of in vivo produced CAP85 as determined from 2-D gels, and the amino acid composition predicted by the clone is a close approximation to that determined from protein compositional analyses. The deduced protein is rich in charged residues (K 15%, D 12%, E 10%, and H 11%), but did not contain either cysteine or tryptophan.

Inspection of the cDNA sequence revealed similarity to the WSP gene family, or more specifically, to Group 2 LEAs. The gene showed a typical Group 2-like 11-residue lysine-rich repeat contained within a larger 22-amino acid sequence that was repeated 11 times within the clone (FIGS. 3A, 3B and 4). The repeats begin at around 300 bp into the 2.0 kb clone and continue to near the stop codon at bp 1640. The repeats are not contiguous but are separated irregularly by spans of 9 to 28 amino acids. Database searches indicated the highest homology to Rab17, which is a Group 2 LEA. Two other imperfect repeating motifs were also found in the primary structure of the deduced protein. Both were interspersed between the lysine repeats. The longer repeat was present 4 times, while the shorter repeat was present 3 times (FIGS. 3A and 3B). CAP85 differs from the Group 2 LEAs in that there is no serine cluster.

Blot of genomic DNA digests. Genomic Southern blots probed with either the PCR clone, pcr733, or the cDNA clone provided insight into the organization of the gene. Both probes produced the same pattern. The hybridization pattern appeared simple, which indicated that CAP85 is present as a single gene or a small gene family.

Increased message and protein levels of CAP85 during cold and water stress. When spinach was subjected to a water stress, there was a dramatic increase in the message levels. The levels of message remained elevated throughout the desiccation stress period. Once the plant was returned to a normal hydrated state, the message levels decreased to non-stressed levels within one day. Spinach also showed an increased abundance of CAP85 protein in response to a water stress. In contrast, the protein levels remained high even after return to a normal hydration state. The protein turn-over rate appeared to be slower than that of the message, as elevated protein levels were evident 24 hours following the return to non-stress conditions. Also, while changes in the protein levels were apparent, the changes in the message abundance were far more pronounced.

The distribution of CAP85 protein and message. The distribution of the protein and the message in spinach seedlings was determined. Protein and RNA were extracted from various tissues from 2 day cold acclimated plants. Immunodetectable protein was found in the leaf, cotyledon, hypocotyl, and root. CAP85 protein was also detected in seeds and pollen. Similarly, the CAP85 message was present in leaf, petiole, and root tissues during cold acclimation. Cell fractionation studies with leaf and hypocotyl tissue showed that CAP85 was present in the cytosol, and possibly in the endoplasmic reticulum and chloroplast.

Boiling solubility of CAP85. Proteins were extracted from 2 day cold acclimated leaf tissues and subjected to 2 and 10 minute boiling treatments. Protein blot analyses confirmed that CAP85 is not rendered insoluble by boiling.

EXAMPLE b 2—Amplification of CAP85 cDNA

Amplification of the cDNA to obtain a CAP85 probe selected for a gene with an orientation which placed the 55-A5' sequence before that of the 50-B3' sequence. In screening the cDNA library with pcr733, we selected for the gene with the 55-A5'→50-B3' arrangement. Both pcr733 and the EDNA clone hybridize, under high stringency, to the gene containing the 55-A5'→→50-B3' orientation, and not the B→A orientation. Even if the two genes encode closely related proteins, the bias of the PCR and cDNA clones would select for only one member of the CAP85 doublet. The match of the cDNA clone to the 55 kDa peptide sequence from CAP85 establishes the linkage of this gene to a protein that is associated with the cold acclimation process. In addition, the amino acid composition of the predicted protein and that of CAP85 are similar, as are the observed and the estimated isoelectric points. Finally, the influences of low temperature and water stress on the abundance of the transcript are consistent with the accumulation of CAP85 in response to these conditions.

EXAMPLE 3—Secondary and Tertiary Structure of CAP 85

For secondary and tertiary structure of the protein, an α-helical structure in the 22-mer lysine repeating motif of CAP85 is suggested. In plotting a 3.6 amino acids/turn α-helix, beginning with the first member of the motif, we observe four distinct faces. The first face is primarily composed of acidic residues ($D_{12}$, $E_5$, $D_{16}$), while the second face is composed of basic residues ($K_6$, $K_{13}$, $K_{17}$). The third face is mostly non-polar residues with adjacent ($E_3$, $K_7$) acidic and basic residues, which can form a salt bridge. Additional salt bridge combinations can act to stabilize the α-helical structure. The final face is a mixture of acid, basic, non-polar, and polar residues. The repeating motif, from residue 1 to 18, forms four complete cycles ending at residue $P_{19}$. Proline is associated with loop structures. The glycine immediately following $P_{19}$ further favors that this part of the peptide is a turn or loop region. The 11 repeating motifs in the α-helical conformation can join in helix-helix associations either along the non-polar regions or in anti-parallel arrangements along the acidic and basic faces. These associations along the non-polar regions permit the charged residues to be free to form interactions with charged cellular components. Such helices can interact with phospholipid head groups of the membrane. In such associations, the formation of ionic interactions between the charged phospholipid head groups and CAP85 can function to stabilize the membrane both during water loss due to dehydration and also exposure to low temperature by acting as a reinforcing lattice network. A coating of CAP85 on the inner face of the plasma membrane can provide a matrix able to stabilize membrane structure during extreme loss of cellular water and volume. These highly hydrophilic proteins participate in adaptive mechanisms in plants during cold and water stress conditions.

EXAMPLE 4—Cloning of CAP160

Antibody screening was used to isolate cDNAs for CAP160. Sixty clones were selected from initial screenings of the same cDNA library used to isolate CAP85. Several of these clones were used for a RNA blot screening to verify that the cDNA corresponded to a gene that was upregulated during cold acclimation. The clones with the largest inserts were further characterized by protein blot analysis of the fusion protein in *E. coli* lysates. Two clones expressed a fusion protein that appeared to be slightly larger than authentic CAP160 obtained from spinach leaf tissue. These clones, along with another lacking 200 bp from the $NH_2$-terminus, were used for sequencing. From sequence analysis, the cDNAs for CAP160 appear to contain full coding sequence for the protein. We were also able to match the deduced amino acid sequence with protein sequence information obtained from sequencing CNBr cleavage products of purified CAP160, firmly establishing the identify of the cDNAs.

Like CAP85, CAP160 has repeating motifs. However, the pattern and sequence of the repeating elements are very different from those of CAP85. The repeats are fewer and larger in CAP160. No significant sequence similarity at the amino acid level appears between CAP160 and CAP85. Only in the carboxyl-termini of both proteins is there significant homology over a short 10-residue region that happens to encompass a lysine repeat of CAP85. Evidence that the cDNAs encode CAP160 include the antibody reactivity, low temperature upregulation, the size of product at roughly 160 kDa by SDS-PAGE, and the cDNA sequence closely matches the amino acid sequence determined from CNBr cleavage fragments of purified CAP160.

We have screened the genomic library for CAP160 clones. Five clones have been isolated and confirmed by PCR with three different sets of CAP160 primers. The clones range from 4 to perhaps greater than 6 kb.

EXAMPLE 5—Insertion of Cold or Drought Tolerance Genes Into Plants

One aspect of the subject invention is the transformation of plants with genes encoding a cold acclimation protein as disclosed herein. The transformed plants are resistant to damage by extreme cold temperatures, freezing, or drought. The transformed plants can be monocots or dicots and, in a preferred embodiment, would be citrus. When transforming monocots, it may be most advantageous to transform embryogenic cells or tissue using DNA bound to high-velocity microprojectiles as a means of delivering it to the embryogenic cells. See for example, Fromm, M. E., F. Morrish, C. Armstrong, R. Williams, J. Thomas, T. M. Klein [1990] "Inheritance of expression of chimeric genes in the progeny of transgenic maize plants," *Bio/Technology* 8:833–839.

Genes encoding cold acclimation proteins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, and the like. Accordingly, the sequence encoding a cold acclimation protein can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System,* Offset-durkkerij Kanters B. V., Alblasserdam, Chapter 5; Fraley et al., *Crit. Rev. Plant Sci.* 4:1–46; and An et al. (1985) EMBO J. 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA A large number of techniques are available for inserting DNA into a plant host cell. Those techniques include transformation with T-DNA using *Agrobactenium lumefaciens* or *Agrobactetium rhizogenes* as transformation agent, fusion, injection, electroporation, or the use of high-velocity microprojectiles, as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al.[1978] *Mol. Gen. Genet.* 163:181–187). The agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobactetium tumefaciens* or *Agrobacterium rhizogenes* for the transfer of the DNA into the plant cell. Alternatively, DNA may be introduced into plant cell suspensions, embryogenic cells, or other embryogenic tissue by one of the methods noted above. Whole plants can then be regenerated from the treated plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands except for a selectable or screenable marker are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

A variety of plants have been genetically transformed according to the above-described methods. These plants include alfalfa, apple, asparagus, broccoli, cabbage, carrot, cauliflower, celery, corn, cotton, cranberry, cucumber, eggplant, flax, grape, horseradish, kiwi fruit, lettuce, muskmelon, oilseed rape, papaya, pea, pepper, plum, poplar, potato, raspberry, rice, rye, soybean, spruce, strawberry, sugarbeet, sugarcane, sunflower, sweet potato, tobacco, tomato, walnut, and wheat (Gasser, C. S., R. T. Fraley [1992] *Scientific American June:*62–69). Other transgenic plants of interest which can be produced are plants included in the family Solanaceae, as well as citrus.

EXAMPLE 6—Enhancement of Cold Tolerance in Microorganisms

The inability of *Escherichia coli* to survive a freeze/thaw cycle is well known. We demonstrated that CAP160 can be expressed in a microorganism and, advantageously, alter its cryotolerance. *Escherichia coli* were transformed with a gene expressing a CAP160 DNA β-galactosidase fusion protein according to methods well known in the art. The survival rate of the transformed *E. coli* cells following a freeze/thaw cycle was compared against cells containing pBluescript plasmid without an insert (wild-type).

XL1-Blue cells containing a pBluescript plasmid with the CAP160 DNA, or without an insert, were grown to midlog phase in an LB/AMP medium at 37° C. Fusion protein expression was induced by addition of IPTG to the culture medium (1 or 10 mM final concentration). The cultures were allowed to incubate for an additional 30 minutes at 37° C. following the addition of IPTG. Aliquots of cells in culture tubes were then equilibrated to −5° C. in a controlled temperature bath and seeded with a chip of sterile ice to initiate freezing of the culture medium. Freezing of the 2 ml culture medium equilibrated to −5° C. was rapid with the transition from liquid to solid phase occurring within a minute. After one hour at −5° C., frozen cells were either maintained at −5° C., or transferred to −20° C. After one hour at −20° C., aliquots of the cells were transferred to −80° C. The rate of cooling from −5° C. to −20° C. and −80° C. was not determined. After 16 hours, the cultures were thawed at 4° C., and survival was determined by dilution series plate counts following overnight growth on LB/AMP agar plates at 37° C. Unfrozen cells kept at 4° C. served as the control. The data, as shown in Table 2, below, are expressed as the percent survival relative to the unfrozen control. The values are the mean±SE of nine separate experiments.

TABLE 2

Survival of recombinant *Escherichia coli* following a freeze/thaw stress

| | Temperature (°C.) | | |
|---|---|---|---|
| | −5 | −20 | −80 |
| pBluescript only | | | |
| −IPTG | 11 ± 4 | 4 ± 2 | 1 ± 1 |
| +IPTG | 10 ± 2 | 3 ± 1 | 1 ± 1 |
| pBluescript w/CAP160 | | | |
| −IPTG | 27 ± 8 | 5 ± 2 | 1 ± 1 |
| +IPTG | 31 ± 9 | 6 ± 1 | 2 ± 1 |

After freezing at −5° C., the survival rate for the cells expressing CAP160 was roughly three-fold higher than the wild-type cells containing pBluescript plasmid only. Induction with IPTG only slightly altered the survival rate in the CAP160 producing cells and had no effect on the others. At temperatures below −5° C., survival of 30 CAP160 cells was slightly higher than that of the cells containing pBluescript only.

To determine the equilibrium freezing $LT_{50}$ (killing temperature for 50% of the cells), cultures induced with IPTG were cooled at 2° C. per hour to −20° C. following the initiation of freezing with a sterile ice chip at −2° C. Survival of frozen cells was determined after exposure to −2, −4, −6, −8, −10, −15, or −20° C. and thawing overnight at 4° C. Cells containing the pBluescript plasmid without an insert lost viability rapidly between −2° and −4° C. (FIG. 5) and yielded an estimated $LT_{50}$ of −3° C. The cells expressing the CAP160 fusion protein showed substantially greater survival following freezing. The estimated $LT_{50}$ of these cells was about −6° C., and between −6° C. and −20° C., their survival rate was between four and seven fold higher than wild-type cells. Clearly, expressing the CAP160 fusion protein enhanced the ability of XL1-Blue cells to survive a freeze/thaw stress.

Figure 5:
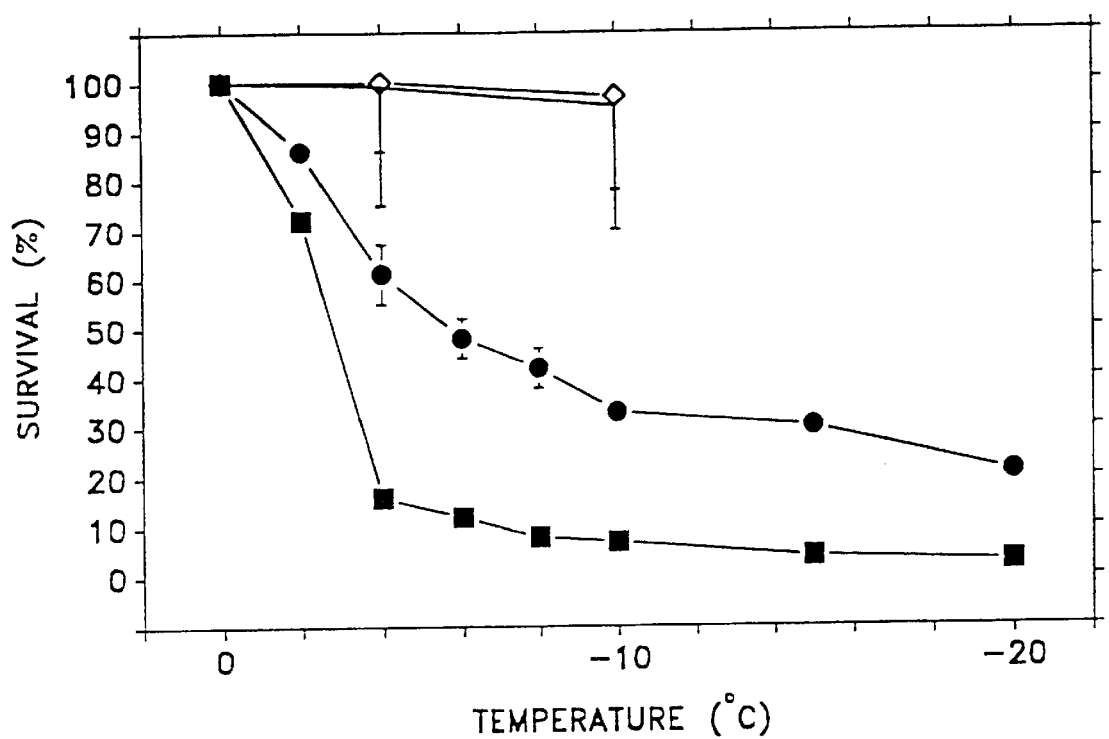
FIG. 5 shows the enhancement of survival rate following a freeze/thaw stress of *Escherichia* coli XL1-Blue cells expressing a fusion protein for spinach CAP160. Squares, wild-type cells containing a pBluescript plasmid without an insert; closed circles, cells containing pBluescript expressing CAP160 fusion protein; diamonds, cells containing a pBluescript without an insert or expressing the CAP160 fusion protein, cooled to –4° C. or –10° C., then warmed to 4° C. without freezing. Percent survival was based on unfrozen control cells that were kept at 4° C.

Freezing is much more deleterious to *E. coli* than chilling and/or supercooling. That CAP160 was protecting against freeze/thaw stress and not against chilling stress was indicated by the near 100% survival rate of cells supercooled to −10° C. and warmed without freezing (FIG. 5).

Other transgenic microorganisms can be produced by methods that are well known and which can be conducted by a person of ordinary skill in the art. These other organisms include other bacteria as well as eukaryotic microorganisms such as yeast.

Homology searches indicate that CAP160, in its entirety, is a novel protein whose biological function cannot be identified by shared homology with known proteins, including antifreeze and ice nucleation proteins that function to alter freezing of water. Thus, CAP160 represents a new class of intracellular low temperature stress proteins with a function linked to enhanced freezing tolerance mechanisms in microorganisms.

EXAMPLE 7—Construction of Chimeric Genes

Any number of structural chimeric cold acclimation genes can be constructed using readily available promoters and polyadenylation signals. One example is to use the cauliflower mosaic virus 35S promoter, which is a strong constitutive promoter, to drive transcription of the cold acclimation gene, and a nopaline synthase polyadenylation signal to ensure the RNA is properly processed and translated into a functional protein (Shah et al. [1986] *Science* 233:478–481). Transformed kanamycin resistant cells can be regenerated into plants and tested for enhanced freezing tolerance. Plants showing enhanced cold tolerance can be analyzed to show that the introduced cold acclimation genes are responsible for the change in hardiness. Promoters for inducible genes can also be used in chimeric cold acclimation gene constructs. Natural promoters for these genes also can be used. This allows the cold acclimation genes to be activated when needed to enhance freezing tolerance at specific times. Other inducible promoters can also be used.

In order to explore the prospect that CAP160 and CAP85 form a complex that requires both proteins for optimum function, plants expressing both spinach proteins can be produced. Two ways to achieve this are to transform transgenic plants already expressing one of the spinach proteins with a construct from the second gene and to make constructs that contain both cDNA sequences that can be co-expressed in transformed plants or, as above, transferred sequentially. In the former case, a second selective media can be employed using the bar gene (Vasil et al. [1992] *Bio/Technology* 10:667–674).

It should be understood that the examples and embodiments described herein are for illustrative purposes only and that various modifications or changes in light thereof will be suggested to persons skilled in the art and are to be included within the spirit and purview of this application and the scope of the appended claims.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1813 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
CACGAGCTAA   TTTGTTGTAA   TCAAGCAATA   ACAATGGCTG   ATGAAAGGAA   CACTTATGGG        60

GGACCCGCAC   CATCTATGGA   GACCACTGAT   CGTGGTATGT   TTGATTTCAT   GAAGAAGAAC       120

AACAAGGGAG   AGGATCACAA   GCCATCCGAG   GCCGATGTGA   TTGCCTCCGG   CGGTATCGGA       180

AAGTTGCCCG   TCTCCGAACC   TGCTCATTAT   GACCATGATG   ACAAGGAACA   TGTTGGACTC       240

CTTGAGAAAA   AACATATTGG   ACTTGTTGAG   CAATTCCATC   GTTCTGATCA   CGCTTCCGAC       300

GAAAGACATC   ATGATGAAGA   GCAAAACAAA   GGTGGTGTCT   TCGGAAAAAT   CAAGGAGAAG       360

CTCCCCGGTC   AGCATGATTC   GGATACTACC   ACACATACAC   AACAATTATA   CCCTGCTTCT       420

GATCATAACT   ACAACACCCA   CCATGTCCAC   CAAGACGATG   AAAAGAAGGA   CAACATCCTT       480

GACAAAATCA   AGGATAAGCT   TCCCGGGAAA   CATGAAGATA   AGAAGCAAGA   CTATCACCAG       540

CACCAAGAGG   AGGAAAAGAA   GGGAGGAGCC   CTTGACAAAA   TCAAGGACAA   GCTGCCCGGT       600

CAGGGTAATG   CTGGACACAC   GCAGCAATTA   TACCCTGCCC   CTGATCATAA   CTACAACACA       660

CACCATGTCC   ACCAAGACGA   GGAAAACAAG   GATAGTGTCT   TAGACAAAAT   CAAGGATAAG       720

CTGCCCGGAC   AACATGAAGA   TAAGAAGAAT   GACTATCACC   ACCACCAAGA   GGAGGAAAAG       780

AAGGATAGTG   TCCTAGACAA   AATCAAGGAT   AAGATGTCCG   GGCAGCATGA   AGATAAGAAG       840

AATGACTATC   ACCACCACCA   AGAGGAGGAA   AAGAAGGGAG   GAGTCCTTGA   CAAAATCAAG       900
```

-continued

```
GACAAGTTGC CTGGTCAACA TGATGCAGAC ACTGCCAGAC ACACGCAGCA ACTATACCCT    960
GCTGCTGATC ATAACTACAA CACACACCAT GTCCACCAAG ATGAGGAAAA CAAGGATAGC   1020
GTCCTTGACA AAATCAAGGA CAAACTACCC GGACAACATG ATGATAAGGC TGCATACTCG   1080
CAACATGACC ACCACAAGCA CCACCAAGAG GAGGAAAACA AGGGTGGAGT CCTCGACAAA   1140
ATCAAGGACA AACTGCCTGG TGTCTACATG GTGGTCAAAC ATGATGGTGA TATTGTCGAA   1200
CACACGCAAC AATTATACCC TGCTCCTGAT CATAACTACA ACACTCACTA TGTCCATGAA   1260
GACGAGAAAA AGAAGGATAG TGTCCTAGAC AAAATCAAGG ACAAGTTACC CGGACAACAT   1320
GAGGAAAAGG CAGCAGCATA CTCTGAGCCA TCATATGATT CACACCCTAC ACCTGCAAAG   1380
CATCATGATT ATTTCCCCCA AGAGGAGGAA AAGAAAGGTG GTGTCATGGA CAAAATTAAG   1440
GACAAGCTTT CCGGCCAACA TAAAGATAAG GCCGACGAGC ATGAGTTGGT TGCTCCGTTG   1500
GTGACAGTCG AACCACATTC TGAGGGTGAT AAGGAAAAGA AGGGGTTCTT GGAGAAGATT   1560
AAGGACAAAA TCCCCGGCCT CCACTCCAAG AATGATGCTG AAGAGAAGAA GACCCATGAG   1620
GAGAAAAAAG AGGGATACTA AACTTAACTA ATAAATATCT ACGTATATTA TGTTCAATAA   1680
GATCGAATTA GTTGCTTTTT TTAGGTTGAT GTGTTTTTCT TGATCAATGC TTTGTGTAAT   1740
TTGAGTCCAA ACTGTGGGGT TTTGATGTCA GTGTTTTTTT CATGACGATG AATATGCAAT   1800
TATGTGTGTA TGG                                                      1813
```

( 2 ) INFORMATION FOR SEQ ID NO:2:

( i ) SEQUENCE CHARACTERISTICS:
    ( A ) LENGTH: 535 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:2:

```
Met Ala Asp Glu Arg Asn Thr Tyr Gly Gly Pro Ala Pro Ser Met Glu
 1               5                  10                  15

Thr Thr Asp Arg Gly Met Phe Asp Phe Met Lys Lys Asn Asn Lys Gly
             20                  25                  30

Glu Asp His Lys Pro Ser Glu Ala Asp Val Ile Ala Ser Gly Gly Ile
         35                  40                  45

Gly Lys Leu Pro Val Ser Glu Pro Ala His Tyr Asp His Asp Lys
     50                  55                  60

Glu His Val Gly Leu Leu Glu Lys Lys His Ile Gly Leu Val Glu Gln
 65                  70                  75                  80

Phe His Arg Ser Asp His Ala Ser Asp Glu Arg His His Asp Glu Glu
                 85                  90                  95

Gln Asn Lys Gly Gly Val Phe Gly Lys Ile Lys Glu Lys Leu Pro Gly
                100                 105                 110

Gln His Asp Ser Asp Thr Thr Thr His Thr Gln Gln Leu Tyr Pro Ala
             115                 120                 125

Ser Asp His Asn Tyr Asn Thr His His Val His Gln Asp Asp Glu Lys
     130                 135                 140

Lys Asp Asn Ile Leu Asp Lys Ile Lys Asp Lys Leu Pro Gly Lys His
145                 150                 155                 160

Glu Asp Lys Lys Gln Asp Tyr His Gln His Gln Glu Glu Glu Lys Lys
                165                 170                 175

Gly Gly Ala Leu Asp Lys Ile Lys Asp Lys Leu Pro Gly Gln Gly Asn
```

-continued

|     |     |     | 180 |     |     |     | 185 |     |     |     | 190 |     |     |
|-----|-----|-----|-----|-----|-----|-----|-----|-----|-----|-----|-----|-----|-----|

Ala Gly His Thr Gln Gln Leu Tyr Pro Ala Pro Asp His Asn Tyr Asn
        195                 200                 205

Thr His His Val His Gln Asp Glu Glu Asn Lys Asp Ser Val Leu Asp
    210             215                 220

Lys Ile Lys Asp Lys Leu Pro Gly Gln His Glu Asp Lys Lys Asn Asp
225             230                 235                         240

Tyr His His His Gln Glu Glu Glu Lys Lys Asp Ser Val Leu Asp Lys
                245             250                         255

Ile Lys Asp Lys Met Ser Gly Gln His Glu Asp Lys Lys Asn Asp Tyr
        260                 265                 270

His His His Gln Glu Glu Glu Lys Lys Gly Gly Val Leu Asp Lys Ile
        275                 280                 285

Lys Asp Lys Leu Pro Gly Gln His Asp Ala Asp Thr Ala Arg His Thr
290                 295                 300

Gln Gln Leu Tyr Pro Ala Ala Asp His Asn Tyr Asn Thr His His Val
305                 310                 315                 320

His Gln Asp Glu Glu Asn Lys Asp Ser Val Leu Asp Lys Ile Lys Asp
                325                 330                 335

Lys Leu Pro Gly Gln His Asp Asp Lys Ala Ala Tyr Ser Gln His Asp
                340                 345                 350

His His Lys His His Gln Glu Glu Glu Asn Lys Gly Gly Val Leu Asp
            355                 360                 365

Lys Ile Lys Asp Lys Leu Pro Gly Val Tyr Met Val Val Lys His Asp
        370                 375                 380

Gly Asp Ile Val Glu His Thr Gln Gln Leu Tyr Pro Ala Pro Asp His
385                 390                 395                 400

Asn Tyr Asn Thr His Tyr Val His Glu Asp Glu Lys Lys Lys Asp Ser
                405             410                 415

Val Leu Asp Lys Ile Lys Asp Lys Leu Pro Gly Gln His Glu Glu Lys
            420                 425                 430

Ala Ala Ala Tyr Ser Glu Pro Ser Tyr Asp Ser His Pro Thr Pro Ala
        435                 440                 445

Lys His His Asp Tyr Phe Pro Gln Glu Glu Glu Lys Lys Gly Gly Val
    450                 455                 460

Met Asp Lys Ile Lys Asp Lys Leu Ser Gly Gln His Lys Asp Lys Ala
465                 470                 475                 480

Asp Glu His Glu Leu Val Ala Pro Leu Val Thr Val Glu Pro His Ser
            485                 490                 495

Glu Gly Asp Lys Glu Lys Lys Gly Phe Leu Glu Lys Ile Lys Asp Lys
            500                 505                 510

Ile Pro Gly Leu His Ser Lys Asn Asp Ala Glu Glu Lys Lys Thr His
        515                 520                 525

Glu Glu Lys Lys Glu Gly Tyr
530                 535

(2) INFORMATION FOR SEQ ID NO:3:

(i) SEQUENCE CHARACTERISTICS:
        (A) LENGTH: 2720 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

| | | | | | | |
|---|---|---|---|---|---|---|
| GCACAAGGTT | ATAACCTCCT | ATTTATTTCC | AATTCAATTT | GTATCTCATT | TTATATAAAT | 60 |
| AGTATTTTCA | ATTAAAAAAA | CCAAGAATTC | AAAATGGAAC | ACCCTAGCGG | TCACACGCGT | 120 |
| CACACTACTC | ATGTAGAAGA | TGATCTTCAA | GATGCTTCCA | TACAAACTGG | TCATAATGAA | 180 |
| GATGAGAAGC | CTGAGAAGAA | AACAATGATG | ATGAAAGTAA | AGGCGAAAGC | AAGGAAGATT | 240 |
| AGAGACAGTA | TTAAGAATGT | TGGACATAGT | CATGATCATG | ATCATGATCA | CGATGAGAAT | 300 |
| GACGACGATG | ATGACGAGGA | GGAGGAAGTT | GAGATGGATA | TGGACTCTGA | AATCCAAGGC | 360 |
| ACTCATACTG | CTCAAACCGG | CACACCAGGG | GAGGAAGTTA | CAAGGCAGAA | GCTGCATGAA | 420 |
| CCAAAACTGG | TAGAAAGAAC | AATAGGTGAA | GATATCCAAG | TTCGGAACAG | ACTAGGTGAT | 480 |
| TATCAGACAT | TTGATCCTAC | TTCTGAAACA | TTCACTCCTG | GACATGATCA | GACCTTAGGT | 540 |
| TGGTCGAGGA | CTGATACCGG | AAAGCCAAAA | GAGTACGGTG | GAAGTCATAG | TACTGAAGCT | 600 |
| TCTGATAAAG | AGATGAATGC | AGCAGCTCCT | GTAAATCTTG | GAGGTGTTGT | TGTTGGTTGT | 660 |
| GACCATCAGG | TCCCGAAAGA | TGTAGGGGAA | GATAGTCATT | CTGCTAATTA | TCAGTCTGAA | 720 |
| GTCATTGAAC | CAACAGTTAC | TGGATTCGAA | TTCCCGGTTG | CTCAAAGTCA | TTCACCAGCA | 780 |
| AATAAGCCAC | AGGGCGATTT | TCAGACCTTT | AATCCTAGGA | CTGATACTGA | AAGGCTAAAC | 840 |
| AAGTCAGTGG | AAATGTTCAA | TGAATCGAAT | AATGCACCAA | TATCAGCCCA | TTCAGGACAT | 900 |
| GAATCACATG | AAAGAACTGC | AATGGAAGGG | GTGGTTGATG | CCCCGGGAAA | CAAGACAGAA | 960 |
| GGCGATTATC | AGACCTTTGA | TCCTAAGTCT | ACAAGCTATG | TTCCCGGACA | AGAAGAGACC | 1020 |
| TTGGGTTGGT | CTAGAACTGA | CACCGGAGGG | CTAAACAAGT | CCGAGGAACT | TTCCAATCTA | 1080 |
| TCGAACAACA | CATCAACTGA | AACTCATTCA | GGTGATGAAG | AAACAAGGAT | TATTCAAATC | 1140 |
| CTGAATCAGA | TGGATTTAAT | GAACGTTAAC | GAAGAATCGC | AGCAGAAACC | AACAGCACCA | 1200 |
| GATGATTCTC | ACCTGAACAA | AACAGAACAT | CATAATCCAC | CAGATGAGAA | AATCTCAACT | 1260 |
| GAAAGCCACC | ATGATCAGTT | CTTTGCAAAG | CCAGACACAT | CTGAGACGGG | CCCAGTTGTT | 1320 |
| CAAGCTACTA | CTACTCCAGC | CACTGATGGT | AATAGCTACA | CCGGAATGAT | ATCAAATGCG | 1380 |
| GCTGCAATGG | TGGCTGATAA | GGCAATGCTA | GCCACTAGTG | CTGTTACATC | AAAGCTAGGG | 1440 |
| TATGGTGGGC | CATCCACCGG | GCCTACTAGT | CCTGATCAGC | AGCACTCAAC | AACTGATGTA | 1500 |
| ACTTCAGAAA | TGCACGACAA | CAACCCGTCA | GATAAGCCCG | TGGGTACTAC | TTATGGGGAG | 1560 |
| AGAATGTCGA | GTGCCACAGC | TGTTGTTACT | GATAAAGCTA | TACAAGCCAA | GGATGTTGTA | 1620 |
| GCCACTAAGC | TAGGCTATGG | TGGCAATCCT | GATCAGCAGC | ACTCCACTGA | TGTGACTTCA | 1680 |
| GAAATGCATG | ATAACCCGTC | AGAGCAGCCC | GTGGGTACTA | CCTACGGGGA | GAAAATATCG | 1740 |
| AGTGCCACGA | CTGTTGTTAC | TGATAAGGCT | ATACAAGCCA | AGGATGTTGT | AGCCGCTAAG | 1800 |
| CTGGGCTATG | GCGGGCCGTC | CACCGGGCCA | TCCACTGGGC | CTATTACCGG | ACCATCCAAG | 1860 |
| GGGCCTATTA | CCGGGCCATC | CACCGGGCCT | ATTACATGGG | GGATAAGGG | AGTGGCAGTG | 1920 |
| AAGGAGTATT | TGGTAGAGAA | ACTGAAGCCC | GGTGAAGATG | ACAAGGCGTT | GTCCGAGGTT | 1980 |
| ATAACTGAAG | CCTTGCCTTC | GCCCTTACAC | AAACCGAAGG | AGGAGGGTGT | GACTATAATA | 2040 |
| GGGAGAGTTG | CAGAGCCTAA | AGAGGTGGTG | CAAATGATTG | ATCATATTGA | GGAGAAGAAT | 2100 |
| GATGATGGTA | TAGTGATGGG | TGAAGATGAC | AAGGCAGTGT | TCGAGGCTGT | AGTTGGGAAG | 2160 |
| GTAGGGGGAG | GGGACGAGGT | TGCGGAAAGG | CTTGGTTGGG | GGAGGAGAA | GAAGGAGGAT | 2220 |
| GGTAGTGATA | ATGGTGGTGC | AGGGGTGGTT | AGTCCAGGGA | AGGGTGTAAT | GGAAAGGATT | 2280 |
| AAAGATGCTG | CTAGTGGGTG | GTTTCAGAGT | AGTGATGACT | TTCCGTCTCA | GGATACCGGT | 2340 |
| ACCCGTACCC | GTCATATCAC | ACAAGGAACG | GAAAGTTTTC | CCATTTCTAG | CATGGAAAGT | 2400 |

```
GAGCAGAAAA GAATCGGTGG TGCAGCGTCT CTTTAGTAAT TTGAGCTTAG ATATGTGTTC      2460

CGGGTCTGGA AGTGGAACTG GGGGATGATC TGGAAGTACC TTGCCCTGTC AAGTAGAGCA      2520

AACGTTAGCC CCACTTTACG ACCCAGTACA ATATGTTGTA TTCCCGGATT TTTTTTATTT      2580

GTGATGTGTA AACAATAGCA GTTTGCTTCA GGAGTAATGC TGCTAGCTTG CTAGGAATGT      2640

ACTTCAAATT AACAACTGTT GTAATTTTGT AAATAAAGAA CTGGACACTT TCCAGAGTTT      2700

GTGAAAAAAA AAAAAAAAA                                                  2720
```

(2) INFORMATION FOR SEQ ID NO:4:

(i) SEQUENCE CHARACTERISTICS:
        (A) LENGTH: 802 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Thr Arg Ala Asn Ser Leu Ala Thr Glu Asp Phe Arg Met Cys Cys Ala
 1               5                  10                  15

Pro Arg Phe Ser Glu Gln Met Glu His Pro Ser Gly His Thr Arg His
            20                  25                  30

Thr Thr His Val Glu Asp Asp Leu Gln Asp Ala Ser Ile Gln Thr Gly
        35                  40                  45

His Asn Glu Asp Glu Lys Pro Glu Lys Lys Thr Met Met Met Lys Val
    50                  55                  60

Lys Ala Lys Ala Arg Lys Ile Arg Asp Ser Ile Lys Asn Val Gly His
65                  70                  75                  80

Ser His Asp His Asp His Asp His Asp Glu Asn Asp Asp Asp Asp Asp
                    85                  90                  95

Glu Glu Glu Glu Val Glu Met Asp Met Asp Ser Glu Ile Gln Gly Thr
               100                 105                 110

His Thr Ala Gln Thr Gly Thr Pro Gly Glu Glu Val Thr Arg Gln Lys
           115                 120                 125

Leu His Glu Pro Lys Leu Val Glu Arg Thr Ile Gly Glu Asp Ile Gln
       130                 135                 140

Val Arg Asn Arg Leu Gly Asp Tyr Gln Thr Phe Asp Pro Thr Ser Glu
145                 150                 155                 160

Thr Phe Thr Pro Gly His Asp Gln Thr Leu Gly Trp Ser Arg Thr Asp
                165                 170                 175

Thr Gly Lys Pro Lys Glu Tyr Gly Gly Ser His Ser Thr Glu Ala Ser
            180                 185                 190

Asp Lys Glu Met Asn Ala Ala Ala Pro Val Asn Leu Gly Gly Val Val
        195                 200                 205

Val Gly Cys Asp His Gln Val Pro Lys Asp Val Gly Glu Asp Ser His
    210                 215                 220

Ser Ala Asn Tyr Gln Ser Glu Val Ile Glu Pro Thr Val Thr Gly Phe
225                 230                 235                 240

Glu Phe Pro Val Ala Gln Ser His Ser Pro Ala Asn Lys Pro Gln Gly
                245                 250                 255

Asp Phe Gln Thr Phe Asn Pro Arg Thr Asp Thr Glu Arg Leu Asn Lys
            260                 265                 270

Ser Val Glu Met Phe Asn Glu Ser Asn Asn Ala Pro Ile Ser Ala His
        275                 280                 285
```

```
Ser  Gly  His  Glu  Ser  His  Glu  Arg  Thr  Ala  Met  Glu  Gly  Val  Val  Asp
     290                 295                 300

Ala  Pro  Gly  Asn  Lys  Thr  Glu  Gly  Asp  Tyr  Gln  Thr  Phe  Asp  Pro  Lys
305                      310                 315                           320

Ser  Thr  Ser  Tyr  Val  Pro  Gly  Gln  Glu  Thr  Leu  Gly  Trp  Ser  Arg
               325                      330                      335

Thr  Asp  Thr  Gly  Gly  Leu  Asn  Lys  Ser  Glu  Glu  Leu  Ser  Asn  Leu  Ser
               340                 345                      350

Asn  Asn  Thr  Ser  Thr  Glu  Thr  His  Ser  Gly  Asp  Glu  Glu  Thr  Arg  Ile
          355                 360                      365

Ile  Gln  Ile  Leu  Asn  Gln  Met  Asp  Leu  Met  Asn  Val  Asn  Glu  Glu  Ser
     370                 375                      380

Gln  Gln  Lys  Pro  Thr  Ala  Pro  Asp  Asp  Ser  His  Leu  Asn  Lys  Thr  Glu
385                      390                      395                      400

His  His  Asn  Pro  Pro  Asp  Glu  Lys  Ile  Ser  Thr  Glu  Ser  His  His  Asp
               405                 410                           415

Gln  Phe  Phe  Ala  Lys  Pro  Asp  Thr  Ser  Glu  Thr  Gly  Pro  Val  Val  Gln
               420                 425                      430

Ala  Thr  Thr  Thr  Pro  Ala  Thr  Asp  Gly  Asn  Ser  Tyr  Thr  Gly  Met  Ile
          435                 440                      445

Ser  Asn  Ala  Ala  Ala  Met  Val  Ala  Asp  Lys  Ala  Met  Leu  Ala  Thr  Ser
     450                 455                      460

Ala  Val  Thr  Ser  Lys  Leu  Gly  Tyr  Gly  Gly  Pro  Ser  Thr  Gly  Pro  Thr
465                      470                      475                      480

Ser  Pro  Asp  Gln  Gln  His  Ser  Thr  Thr  Asp  Val  Thr  Ser  Glu  Met  His
               485                      490                      495

Asp  Asn  Asn  Pro  Ser  Asp  Lys  Pro  Val  Gly  Thr  Thr  Tyr  Gly  Glu  Arg
               500                      505                      510

Met  Ser  Ser  Ala  Thr  Ala  Val  Val  Thr  Asp  Lys  Ala  Ile  Gln  Ala  Lys
          515                      520                      525

Asp  Val  Val  Ala  Thr  Lys  Leu  Gly  Tyr  Gly  Gly  Asn  Pro  Asp  Gln  Gln
     530                      535                      540

His  Ser  Thr  Asp  Val  Thr  Ser  Glu  Met  His  Asp  Asn  Pro  Ser  Glu  Gln
545                      550                      555                      560

Pro  Val  Gly  Thr  Thr  Tyr  Gly  Glu  Lys  Ile  Ser  Ser  Ala  Thr  Thr  Val
                    565                 570                      575

Val  Thr  Asp  Lys  Ala  Ile  Gln  Ala  Lys  Asp  Val  Val  Ala  Ala  Lys  Leu
               580                      585                      590

Gly  Tyr  Gly  Gly  Pro  Ser  Thr  Gly  Pro  Ser  Thr  Gly  Pro  Ile  Thr  Gly
          595                      600                      605

Pro  Ser  Lys  Gly  Pro  Ile  Thr  Gly  Pro  Ser  Thr  Gly  Pro  Ile  Thr  Trp
     610                      615                      620

Gly  Asp  Lys  Gly  Val  Ala  Val  Lys  Glu  Tyr  Leu  Val  Glu  Lys  Leu  Lys
625                      630                      635                      640

Pro  Gly  Glu  Asp  Asp  Lys  Ala  Leu  Ser  Glu  Val  Ile  Thr  Glu  Ala  Leu
                    645                 650                      655

Pro  Ser  Pro  Leu  His  Lys  Pro  Lys  Glu  Gly  Val  Thr  Ile  Ile  Gly
               660                 665                      670

Arg  Val  Ala  Glu  Pro  Lys  Glu  Val  Val  Gln  Met  Ile  Asp  His  Ile  Glu
          675                 680                      685

Glu  Lys  Asn  Asp  Asp  Gly  Ile  Val  Met  Gly  Glu  Asp  Asp  Lys  Ala  Val
          690                 695                      700

Phe  Glu  Ala  Val  Val  Gly  Lys  Val  Gly  Gly  Gly  Asp  Glu  Val  Ala  Glu
705                      710                      715                      720
```

```
Arg  Leu  Gly  Trp  Gly  Glu  Glu  Lys  Lys  Glu  Asp  Gly  Ser  Asp  Asn  Gly
                    725                      730                     735

Gly  Ala  Gly  Val  Val  Ser  Pro  Gly  Lys  Gly  Val  Met  Glu  Arg  Ile  Lys
                740                      745                     750

Asp  Ala  Ala  Ser  Gly  Trp  Phe  Gln  Ser  Ser  Asp  Asp  Phe  Pro  Ser  Gln
          755                     760                     765

Asp  Thr  Gly  Thr  Arg  Thr  Arg  His  Ile  Thr  Gln  Gly  Thr  Glu  Ser  Phe
     770                     775                     780

Pro  Ile  Ser  Ser  Met  Glu  Ser  Glu  Gln  Lys  Arg  Ile  Gly  Gly  Ala  Gly
785                      790                     795                     800

Ser  Leu
```

( 2 ) INFORMATION FOR SEQ ID NO:5:

( i ) SEQUENCE CHARACTERISTICS:
       ( A ) LENGTH: 24 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:5:

ATGAAGAAGA AYAAYAAGGG YGAG                                              24

( 2 ) INFORMATION FOR SEQ ID NO:6:

( i ) SEQUENCE CHARACTERISTICS:
       ( A ) LENGTH: 23 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:6:

TARTCRTTCT TCTTRTCCTC RTG                                               23

We claim:

1. An isolated DNA molecule comprising a nucleotide sequence encoding a protein which enhances cold tolerance of a plant cell, wherein said protein is CAP85 having an amino acid sequence as given in SEQ ID NO:2 or CAP160 having an amino acid sequence as given in SEQ ID NO:4.

2. The DNA molecule of claim 1, wherein the encoded protein is CAP85.

3. The DNA molecule of claim 2, wherein the nucleotide sequence encoding the CAP85 protein is as given in SEQ ID NO:1, from nucleotide 34 to nucleotide 1648.

4. The DNA molecule of claim 1, wherein the encoded protein is CAP160.

5. The DNA molecule of claim 4, wherein the nucleotide sequence encoding the CAP160 protein is as given in SEQ ID NO:3.

6. A process for enhancing cold tolerance of a cell, wherein said process comprises the step of transforming said cell with a DNA molecule comprising a coding sequence for a cold acclimation protein selected from the group consisting of CAP85 having an amino acid sequence as given in SEQ ID NO:2 and CAP160 having an amino acid sequence as given in SEQ ID NO:4, wherein expression of said coding sequence results in enhanced cold tolerance of said cell.

7. The process, according to claim 6, wherein said cell is a plant cell.

8. The process, according to claim 7, wherein said plant cell is a cell of a plant of the family Solanaceae.

9. The process, according to claim 7, wherein said plant cell is a citrus plant cell.

10. The process, according to claim 6, Wherein said cell is a bacterium.

11. The process, according to claim 6, wherein said cell is a yeast cell.

12. A transformed cell, wherein said cell is transformed according to the process of claim 6.

13. The transformed cell, according to claim 12, wherein said cell is a plant cell.

14. The transformed cell, according to claim 13, wherein said plant cell is a citrus plant cell.

* * * * *

UNITED STATES PATENT AND TRADEMARK OFFICE
CERTIFICATE OF CORRECTION

PATENT NO. : 5,837,545

DATED : November 17, 1998

INVENTOR(S) : Guy et al.

It is certified that error appears in the above-identified patent and that said Letters Patent is hereby corrected as shown below:

Under "Other Publications":

On the cover page, in the first Guy reference, third line, replace "Rhysiol." with --Physiol.--.

On the cover page, in the second Guy reference, first line, replace "Hakell" with --Haskell--.

On the cover page, in the Hughes reference, second line, replace "Introductionof" with
--Introduction of--.

On the second page, in the Lang reference, first line, replace "terperature" with --temperature--.

In col. 4, line 24, replace "MIRNA" with --mRNA--.

In col. 6, line 40, replace "thymnine" with --thymine--.

In col. 9, line 55, replace *"Modem"* with --*Modern*--.

In col. 10, line 25, replace "ration" with --ratio--.

In col. 14, line 48, replace "EXAMPLE b2" with --EXAMPLE 2--.

In col. 14, line 54, replace "EDNA" with --cDNA--.

UNITED STATES PATENT AND TRADEMARK OFFICE
CERTIFICATE OF CORRECTION

PATENT NO. : 5,837,545

DATED : November 17, 1998

INVENTOR(S) : Guy et al.

It is certified that error appears in the above-identified patent and that said Letters Patent is hereby corrected as shown below:

In col. 21, under the sequence characteristics of SEQ NO:2, after "STRANDEDNESS" replace "single" with --not relevant--; and after "TOPOLOGY" replace "linear" with --unknown--.

Replace SEQ ID NOS: 3, 4, 5 and 6 with the following:

(2) INFORMATION FOR SEQ ID NO:3:

(i) SEQUENCE CHARACTERISTICS:
        (A) LENGTH: 2721 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:3:

```
GCACAAGGTT ATAACCTCCT ATTTATTTCC AATTCAATTT GTATCTCATT TTATATAAAT      60

AGTATTTTCA ATTAAAAAAA CCAAGAATTC AAAATGGAAC ACCCTAGCGG TCACACGCGT     120

CACACTACTC ATGTAGAAGA TGATCTTCAA GATGCTTCCA TACAAACTGG TCATAATGAA     180

GATGAGAAGC CTGAGAAGAA AACAATGATG ATGAAAGTAA AGGCGAAAGC AAGGAAGATT     240
```

UNITED STATES PATENT AND TRADEMARK OFFICE
CERTIFICATE OF CORRECTION

PATENT NO.   : 5,837,545                    Page 3 of 12

DATED        : November 17, 1998

INVENTOR(S)  : Guy et a.

It is certified that error appears in the above-identified patent and that said Letters Patent is hereby corrected as shown below:

| | | | | | |
|---|---|---|---|---|---|
| AGAGACAGTA | TTAAGAATGT | TGGACATAGT | CATGATCATG | ATCATGATCA | CGATGAGAAT | 300 |
| GACGACGATG | ATGACGAGGA | GGAGGAAGTT | GAGATGGATA | TGGACTCTGA | AATCCAAGGC | 360 |
| ACTCATACTG | CTCAAACCGG | CACACCAGGG | GAGGAAGTTA | CAAGGCAGAA | GCTGCATGAA | 420 |
| CCAAAACTGG | TAGAAAGAAC | AATAGGTGAA | GATATCCAAG | TTCGGAACAG | ACTAGGTGAT | 480 |
| TATCAGACAT | TTGATCCTAC | TTCTGAAACA | TTCACTCCTG | GACATGATCA | GACCTTAGGT | 540 |
| TGGTCGAGGA | CTGATACCGG | AAAGCCAAAA | GAGTACGGTG | GAAGTCATAG | TACTGAAGCT | 600 |
| TCTGATAAAG | AGATGAATGC | AGCAGCTCCT | GTAAATCTTG | GAGGTGTTGT | TGTTGGTTGT | 660 |
| GACCATCAGG | TCCCGAAAGA | TGTAGGGGAA | GATAGTCATT | CTGCTAATTA | TCAGTCTGAA | 720 |
| GTCATTGAAC | CAACAGTTAC | TGGATTCGAA | TTCCCGGTTG | CTCAAAGTCA | TTCACCAGCA | 780 |
| AATAAGCCAC | AGGGCGATTT | TCAGACCTTT | AATCCTAGGA | CTGATACTGA | AAGGCTAAAC | 840 |
| AAGTCAGTGG | AAATGTTCAA | TGAATCGAAT | AATGCACCAA | TATCAGCCCA | TTCAGGACAT | 900 |
| GAATCACATG | AAAGAACTGC | AATGGAAGGG | GTGGTTGATG | CCCCGGGAAA | CAAGACAGAA | 960 |
| GGCGATTATC | AGACCTTTGA | TCCTAAGTCT | ACAAGCTATG | TTCCCGGACA | AGAAGAGACC | 1020 |
| TTGGGTTGGT | CTAGAACTGA | CACCGGAGGG | CTAAACAAGT | CCGAGGAACT | TTCCAATCTA | 1080 |

UNITED STATES PATENT AND TRADEMARK OFFICE
CERTIFICATE OF CORRECTION

PATENT NO. : 5,837,545　　　　　　　　　　Page 4 of 12

DATED : November 17, 1998

INVENTOR(S) : Guy et al.

It is certified that error appears in the above-identified patent and that said Letters Patent is hereby corrected as shown below:

```
TCGAACAACA CATCAACTGA AACTCATTCA GGTGATGAAG AAACAAGGAT TATTCAAATC   1140

CTGAATCAGA TGGATTTAAT GAACGTTAAC GAAGAATCGC AGCAGAAACC AACAGCACCA   1200

GATGATTCTC ACCTGAACAA AACAGAACAT CATAATCCAC CAGATGAGAA AATCTCAACT   1260

GAAAGCCACC ATGATCAGTT CTTTGCAAAG CCAGACACAT CTGAGACGGG CCCAGTTGTT   1320

CAAGCTACTA CTACTCCAGC CACTGATGGT AATAGCTACA CCGGAATGAT ATCAAATGCG   1380

GCTGCAATGG TGGCTGATAA GGCAATGCTA GCCACTAGTG CTGTTACATC AAAGCTAGGG   1440

TATGGTGGGC CATCCACCGG GCCTACTAGT CCTGATCAGC AGCACTCAAC AACTGATGTA   1500

ACTTCAGAAA TGCACGACAA CAACCCGTCA GATAAGCCCG TGGGTACTAC TTATGGGGAG   1560

AGAATGTCGA GTGCCACAGC TGTTGTTACT GATAAAGCTA TACAAGCCAA GGATGTTGTA   1620

GCCACTAAGC TAGGCTATGG TGGCAATCCT GATCAGCAGC ACTCCACTGA TGTGACTTCA   1680

GGAAATGCAT GATAACCCGT CAGAGCAGCC CGTGGGTACT ACCTACGGGG AGAAAATATC   1740

GAGTGCCACG ACTGTTGTTA CTGATAAGGC TATACAAGCC AAGGATGTTG TAGCCGCTAA   1800

GCTGGGCTAT GGCGGGCCGT CCACCGGGCC ATCCACTGGG CCTATTACCG GACCATCCAA   1860

GGGGCCTATT ACCGGGCCAT CCACCGGGCC TATTACATGG GGGGATAAGG GAGTGGCAGT   1920

GAAGGAGTAT TTGGTAGAGA AACTGAAGCC CGGTGAAGAT GACAAGGCGT TGTCCGAGGT   1980
```

UNITED STATES PATENT AND TRADEMARK OFFICE
CERTIFICATE OF CORRECTION

PATENT NO. : 5,837,545　　　　　　　　　　Page 5 of 12

DATED : November 17, 1998

INVENTOR(S) : Guy et al.

It is certified that error appears in the above-identified patent and that said Letters Patent is hereby corrected as shown below:

```
TATAACTGAA GCCTTGCCTT CGCCCTTACA CAAACCGAAG GAGGAGGGTG TGACTATAAT    2040

AGGGAGAGTT GCAGAGCCTA AAGAGGTGGT GCAAATGATT GATCATATTG AGGAGAAGAA    2100

TGATGATGGT ATAGTGATGG GTGAAGATGA CAAGGCAGTG TTCGAGGCTG TAGTTGGGAA    2160

GGTAGGGGGA GGGGACGAGG TTGCGGAAAG GCTTGGTTGG GGGGAGGAGA AGAAGGAGGA    2220

TGGTAGTGAT AATGGTGGTG CAGGGGTGGT TAGTCCAGGG AAGGGTGTAA TGGAAAGGAT    2280

TAAAGATGCT GCTAGTGGGT GGTTTCAGAG TAGTGATGAC TTTCCGTCTC AGGATACCGG    2340

TACCCGTACC CGTCATATCA CACAAGGAAC GGAAAGTTTT CCCATTTCTA GCATGGAAAG    2400

TGAGCAGAAA AGAATCGGTG GTGCAGCGTC TCTTTAGTAA TTTGAGCTTA GATATGTGTT    2460

CCGGGTCTGG AAGTGGAACT GGGGGATGAT CTGGAAGTAC CTTGCCCTGT CAAGTAGAGC    2520

AAACGTTAGC CCCACTTTAC GACCCAGTAC AATATGTTGT ATTCCCGGAT TTTTTTTATT    2580

TGTGATGTGT AAACAATAGC AGTTTGCTTC AGGAGTAATG CTGCTAGCTT GCTAGGAATG    2640

TACTTCAAAT TAACAACTGT TGTAATTTTG TAAATAAAGA ACTGGACACT TTCCAGAGTT    2700

TGTGAAAAAA AAAAAAAAA A                                                2721
```

UNITED STATES PATENT AND TRADEMARK OFFICE
CERTIFICATE OF CORRECTION

PATENT NO. : 5,837,545          Page 6 of 12

DATED : November 17, 1998

INVENTOR(S) : Guy et al.

It is certified that error appears in the above-identified patent and that said Letters Patent is hereby corrected as shown below:

(2) INFORMATION FOR SEQ ID NO:4:

(i) SEQUENCE CHARACTERISTICS:
        (A) LENGTH: 780 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:4:

```
Met Glu His Pro Ser Gly His Thr Arg His Thr Thr His Val Glu Asp
1               5                   10                  15

Asp Leu Gln Asp Ala Ser Ile Gln Thr Gly His Asn Glu Asp Glu Lys
                20                  25                  30

Pro Glu Lys Lys Thr Met Met Met Lys Val Lys Ala Lys Ala Arg Lys
                35                  40                  45

Ile Arg Asp Ser Ile Lys Asn Val Gly His Ser His Asp His Asp His
    50                  55                  60

Asp His Asp Glu Asn Asp Asp Asp Asp Glu Glu Glu Glu Val Glu
65                  70                  75                  80

Met Asp Met Asp Ser Glu Ile Gln Gly Thr His Thr Ala Gln Thr Gly
                85                  90                  95
```

UNITED STATES PATENT AND TRADEMARK OFFICE
CERTIFICATE OF CORRECTION

PATENT NO. : 5,837,545  Page 7 of 12

DATED : November 17, 1998

INVENTOR(S) : Guy et al.

It is certified that error appears in the above-identified patent and that said Letters Patent is hereby corrected as shown below:

```
Thr Pro Gly Glu Glu Val Thr Arg Gln Lys Leu His Glu Pro Lys Leu
            100                 105                 110

Val Glu Arg Thr Ile Gly Glu Asp Ile Gln Val Arg Asn Arg Leu Gly
            115                 120                 125

Asp Tyr Gln Thr Phe Asp Pro Thr Ser Glu Thr Phe Thr Pro Gly His
            130                 135                 140

Asp Gln Thr Leu Gly Trp Ser Arg Thr Asp Thr Gly Lys Pro Lys Glu
145                 150                 155                 160

Tyr Gly Gly Ser His Ser Thr Glu Ala Ser Asp Lys Glu Met Asn Ala
                165                 170                 175

Ala Ala Pro Val Asn Leu Gly Gly Val Val Val Gly Cys Asp His Gln
            180                 185                 190

Val Pro Lys Asp Val Gly Glu Asp Ser His Ser Ala Asn Tyr Gln Ser
            195                 200                 205

Glu Val Ile Glu Pro Thr Val Thr Gly Phe Glu Phe Pro Val Ala Gln
            210                 215                 220

Ser His Ser Pro Ala Asn Lys Pro Gln Gly Asp Phe Gln Thr Phe Asn
225                 230                 235                 240

Pro Arg Thr Asp Thr Glu Arg Leu Asn Lys Ser Val Glu Met Phe Asn
                245                 250                 255
```

UNITED STATES PATENT AND TRADEMARK OFFICE
CERTIFICATE OF CORRECTION

PATENT NO. : 5,837,545

DATED : November 17, 1998

INVENTOR(S) : Guy et al.

It is certified that error appears in the above-identified patent and that said Letters Patent is hereby corrected as shown below:

```
Glu Ser Asn Asn Ala Pro Ile Ser Ala His Ser Gly His Glu Ser His
            260                 265                 270

Glu Arg Thr Ala Met Glu Gly Val Val Asp Ala Pro Gly Asn Lys Thr
        275                 280                 285

Glu Gly Asp Tyr Gln Thr Phe Asp Pro Lys Ser Thr Ser Tyr Val Pro
    290                 295                 300

Gly Gln Glu Glu Thr Leu Gly Trp Ser Arg Thr Asp Thr Gly Gly Leu
305                 310                 315                 320

Asn Lys Ser Glu Glu Leu Ser Asn Leu Ser Asn Asn Thr Ser Thr Glu
            325                 330                 335

Thr His Ser Gly Asp Glu Glu Thr Arg Ile Ile Gln Ile Leu Asn Gln
            340                 345                 350

Met Asp Leu Met Asn Val Asn Glu Glu Ser Gln Gln Lys Pro Thr Ala
            355                 360                 365

Pro Asp Asp Ser His Leu Asn Lys Thr Glu His His Asn Pro Pro Asp
            370                 375                 380

Glu Lys Ile Ser Thr Glu Ser His His Asp Gln Phe Phe Ala Lys Pro
385                 390                 395                 400

Asp Thr Ser Glu Thr Gly Pro Val Val Gln Ala Thr Thr Thr Pro Ala
            405                 410                 415

Thr Asp Gly Asn Ser Tyr Thr Gly Met Ile Ser Asn Ala Ala Ala Met
            420                 425                 430
```

UNITED STATES PATENT AND TRADEMARK OFFICE
CERTIFICATE OF CORRECTION

PATENT NO. : 5,837,545

DATED : November 17, 1998

INVENTOR(S) : Guy et al.

It is certified that error appears in the above-identified patent and that said Letters Patent is hereby corrected as shown below:

```
Val Ala Asp Lys Ala Met Leu Ala Thr Ser Ala Val Thr Ser Lys Leu
        435             440             445

Gly Tyr Gly Gly Pro Ser Thr Gly Pro Thr Ser Pro Asp Gln Gln His
        450             455             460

Ser Thr Thr Asp Val Thr Ser Glu Met His Asp Asn Asn Pro Ser Asp
465             470             475             480

Lys Pro Val Gly Thr Thr Tyr Gly Glu Arg Met Ser Ser Ala Thr Ala
            485             490             495

Val Val Thr Asp Lys Ala Ile Gln Ala Lys Asp Val Val Ala Thr Lys
        500             505             510

Leu Gly Tyr Gly Gly Asn Pro Asp Gln Gln His Ser Thr Asp Val Thr
        515             520             525

Ser Glu Met His Asp Asn Pro Ser Glu Gln Pro Val Gly Thr Thr Tyr
    530             535             540

Gly Glu Lys Ile Ser Ser Ala Thr Thr Val Val Thr Asp Lys Ala Ile
545             550             555             560

Gln Ala Lys Asp Val Val Ala Ala Lys Leu Gly Tyr Gly Gly Pro Ser
            565             570             575

Thr Gly Pro Ser Thr Gly Pro Ile Thr Gly Pro Ser Lys Gly Pro Ile
            580             585             590

Thr Gly Pro Ser Thr Gly Pro Ile Thr Trp Gly Asp Lys Gly Val Ala
            595             600             605
```

UNITED STATES PATENT AND TRADEMARK OFFICE
CERTIFICATE OF CORRECTION

PATENT NO. : 5,837,545  Page 10 of 12

DATED : November 17, 1998

INVENTOR(S) : Guy et al.

It is certified that error appears in the above-identified patent and that said Letters Patent is hereby corrected as shown below:

```
Val Lys Glu Tyr Leu Val Glu Lys Leu Lys Pro Gly Glu Asp Asp Lys
    610             615             620
Ala Leu Ser Glu Val Ile Thr Glu Ala Leu Pro Ser Pro Leu His Lys
625                 630             635                     640
Pro Lys Glu Glu Gly Val Thr Ile Ile Gly Arg Val Ala Glu Pro Lys
                645             650                 655
Glu Val Val Gln Met Ile Asp His Ile Glu Glu Lys Asn Asp Asp Gly
                660             665                 670
Ile Val Met Gly Glu Asp Asp Lys Ala Val Phe Glu Ala Val Val Gly
        675             680                 685
Lys Val Gly Gly Gly Asp Glu Val Ala Glu Arg Leu Gly Trp Gly Glu
    690                 695             700
Glu Lys Lys Glu Asp Gly Ser Asp Asn Gly Gly Ala Gly Val Val Ser
705                 710             715                     720
Pro Gly Lys Gly Val Met Glu Arg Ile Lys Asp Ala Ala Ser Gly Trp
                725             730                 735
Phe Gln Ser Ser Asp Asp Phe Pro Ser Gln Asp Thr Gly Thr Arg Thr
            740             745                 750
Arg His Ile Thr Gln Gly Thr Glu Ser Phe Pro Ile Ser Ser Met Glu
            755             760                 765
Ser Glu Gln Lys Arg Ile Gly Gly Ala Gly Ser Leu
    770             775             780
```

UNITED STATES PATENT AND TRADEMARK OFFICE
CERTIFICATE OF CORRECTION

PATENT NO. : 5,837,545            Page 11 of 12

DATED : November 17, 1998

INVENTOR(S) : Guy et al.

It is certified that error appears in the above-identified patent and that said Letters Patent is hereby corrected as shown below:

```
(2) INFORMATION FOR SEQ ID NO:5:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide."

(iii) HYPOTHETICAL: NO (xi) SEQUENCE DESCRIPTION: SEQ ID NO:5:

ATGAAGAAGA AYAAYAAGGG YGAG                                          24
```

UNITED STATES PATENT AND TRADEMARK OFFICE
CERTIFICATE OF CORRECTION

PATENT NO. : 5,837,545
DATED : Nov. 17, 1998
INVENTOR(S) : Guy et al.

It is certified that error appears in the above-identified patent and that said Letters Patent is hereby corrected as shown below:

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

Signed and Sealed this

Twenty-first Day of March, 2000

Attest:

Attesting Officer

Q. TODD DICKINSON

Commissioner of Patents and Trademarks